US010751193B2

(12) United States Patent
Billon et al.

(10) Patent No.: US 10,751,193 B2
(45) Date of Patent: Aug. 25, 2020

(54) DEVICE FOR PERCUTANEOUS TRANSPEDICULAR FUSION

(71) Applicant: CLARIANCE, Beaurains (FR)

(72) Inventors: Adrien Billon, Achicourt (FR); Afshin Gangi, Lahr (FR); Jean Yves Leroy, Campagne-les-Hesdin (FR); Sebastien Schuller, Strasbourg (FR); Guy Viart, Saint Leger (FR); Jean Paul Steib, Strasbourg (FR); Christian Mazel, Le Plessis Robinson (FR); Nicolas Virgaux, Paris (FR)

(73) Assignee: CLARIANCE, Beaurains (FR)

( * ) Notice: Subject to any disclaimer, the term of this patent is extended or adjusted under 35 U.S.C. 154(b) by 434 days.

(21) Appl. No.: 15/131,474

(22) Filed: Apr. 18, 2016

(65) Prior Publication Data

US 2016/0302936 A1    Oct. 20, 2016

Related U.S. Application Data

(60) Provisional application No. 62/148,356, filed on Apr. 16, 2015.

(51) Int. Cl.
*A61F 2/44* (2006.01)
*A61B 17/16* (2006.01)
*A61B 17/88* (2006.01)
*A61F 2/46* (2006.01)

(52) U.S. Cl.
CPC .......... *A61F 2/442* (2013.01); *A61B 17/1642* (2013.01); *A61B 17/1671* (2013.01); *A61B 17/8816* (2013.01); *A61B 17/8819* (2013.01); *A61B 17/8897* (2013.01); *A61F 2/4455* (2013.01); *A61F 2/4611* (2013.01);
(Continued)

(58) Field of Classification Search
CPC ......... A61F 2017/00261; A61F 2/4644; A61B 17/1642; A61B 17/7074; A61B 17/7092–17/7097
See application file for complete search history.

(56) References Cited

U.S. PATENT DOCUMENTS

| 2004/0092933 A1* | 5/2004 | Shaolian | A61B 17/1617 606/279 |
| 2010/0082033 A1* | 4/2010 | Germain | A61B 17/1642 606/79 |

(Continued)

*Primary Examiner* — Matthew J Lawson
(74) *Attorney, Agent, or Firm* — Nixon & Vanderhye

(57) ABSTRACT

A device for percutaneous transpedicular fusion includes at least two straight pedicular cannulas arranged respectively on the upper or lower vertebra, or on the two vertebrae of the spinal segment, at least one guide pin with a curved profile, which is implanted in the endplate of the corresponding vertebra through the corresponding pedicular cannula, of a flexible cannulated drill bit guided around the corresponding guide pin and driven in back and forth movements by a cannulated drive system to nibble out gradually slots in the lower and upper endplate of each vertebra and reduce to flaps the nucleic tissues of an intervertebral disk for the production of the intersomatic space, of an injection device connected to one of the straight pedicular cannulas for the injection of the graft into the intersomatic space, and closing devices that are screwed into the holes left free after retraction of the straight pedicular cannulas.

11 Claims, 23 Drawing Sheets

(52) U.S. Cl.
  CPC ............... *A61F 2210/0085* (2013.01); *A61F 2310/00359* (2013.01)

(56) References Cited

U.S. PATENT DOCUMENTS

| | | | |
|---|---|---|---|
| 2010/0114098 A1* | 5/2010 | Carl | A61B 17/1642 606/80 |
| 2012/0191094 A1* | 7/2012 | Alain | A61B 17/1642 606/80 |
| 2012/0191095 A1* | 7/2012 | Burger | A61B 17/1642 606/80 |
| 2014/0316413 A1* | 10/2014 | Burger | A61B 17/1642 606/80 |
| 2017/0202567 A1* | 7/2017 | Griffiths | A61B 17/1637 |

\* cited by examiner

DEVICE FOR PERCUTANEOUS TRANSPEDICULAR FUSION

The present invention relates to a device for transpedicular fusion enabling the placement and the injection of an autologous or biological graft into an intersomatic space Es that has been arranged beforehand between two upper and lower vertebrae Va, Vb of a spinal segment, in order to bring about an intersomatic fusion by an entirely percutaneous transpedicular approach.

For some years, surgeons working in the spinal surgery field have expressed a keen interest in simple, reliable and rapid techniques for the fusion of a spinal segment, for example.

Currently, surgeons use a so-called open-surgery technique that requires a very large incision to access the area to be treated and to have a direct view. The trauma suffered by the patient is serious, in particular in connection with dissection/deinsertion of tissues, blood loss, and incision length. Open surgery requires a short operating time (because the technique has been mastered), but a long hospitalization time. The associated health care costs are very high.

Surgeons are looking in the spinal surgery field for so-called minimally invasive (MIS) techniques in order to make it possible for the patients to recover more rapidly after a surgical operation. These operating techniques make it possible to reduce the hospitalization time and to promote a rapid return to normal activity, which leads to a significant reduction in health care costs.

Within the field of the so-called minimally invasive (MIS) spinal surgery techniques, it is possible to specify the different access routes and minimal access (MAS) and percutaneous surgeries.

Minimal access surgery (MAS) takes up again the principle of minimally invasive surgery (MIS) using smaller incisions that are maximally opened with special instrumentation. The surgeon has direct visual or endoscopic control of the area to be treated.

In percutaneous surgery, rather than making small incisions, access is gained into the body of the patients by means of holes in the skin through which cannulas are inserted. The cannulas constitute secure routes for the instruments up to the area to be treated. All the insertions of instruments and the extraction of tissues are done through these cannulas. The damages suffered by the patient are thus considerably reduced, but no direct visual control is possible. The increased use of fluoroscopy is associated with serious radiological risks for the surgeons and the patients.

So-called minimally invasive surgery (MIS) techniques using posterior access routes that are simpler and more common are known. These techniques consist in placing fixations consisting of linking rods immobilized in transpedicular polyaxial screws that have been anchored beforehand in the vertebral bodies.

One notes that these techniques by minimally invasive (MIS) posterior route do not make it possible to place a postero-lateral graft as used in open surgery.

In general, the graft is placed by the positioning of an intersomatic cage between the vertebral bodies of two vertebrae overlying and underlying vertebrae, said intersomatic cage being introduced through an additional posterior access route using minimal access surgery (MAS).

This posterior access route using minimal access surgery (MAS) is inconvenient and results in the loss of the benefit of the so-called minimally invasive surgery (MIS) techniques.

On the other hand, the difficult access by the posterior access route makes difficult the preparation of the operation site and the revivification of the vertebral endplates that is needed for a vascularization of the graft. This difficulty of access can lead to a non-negligible rate of fusion failure.

One notes that all these disadvantages slow the development of this so-called minimally invasive surgery (MIS) technique, in spite of its very high promise.

In addition, it is observed that the considerable decrease in traumatic effects that exist with the use of the so-called open surgery techniques, and the maximum reduction of the access routes (reduction of the perforations needed to reach the site to be treated) promote rapid recovery of the patients, a reduced hospitalization time, and a rapid return to normal activity.

The object of the present invention consists in proposing a device for transpedicular fusion enabling the placement and the injection of an autologous and biological graft into an intersomatic space arranged beforehand between two upper and lower vertebrae Va, Vb of a spinal segment, in order to bring about an intersomatic fusion by an entirely percutaneous transpedicular approach.

The transpedicular fusion device according to the present invention consists of at least two straight pedicular cannulas arranged respectively on the upper vertebra Va or on the lower vertebra Vb, or on the two vertebrae Va, Vb of the spinal segment, and constituting secure work channels and sighting positioner, of at least one guide pin with a curved profile, which is implanted in the endplate Pi, Ps of the corresponding vertebra Va, Vb through the corresponding pedicular cannula, of a flexible cannulated drill bit guided around the corresponding guide pin and driven in back and forth movements by a cannulated drive system so as to nibble out gradually and in a controlled manner slots F in said lower endplate Pi and upper endplate Ps of each vertebra Va, Vb and so as to reduce to flaps the nucleic tissues of an intervertebral disk D for the production of the intersomatic space Es, of an injection device connected to one of the straight pedicular cannulas for the injection of the graft into the intersomatic space Es thus produced, and of closing devices that are screwed into the holes left free after the retraction of said straight pedicular cannulas.

The transpedicular fusion device according to the present invention comprises a flexible cannulated drill bit including a rigid cannulated rod extended by a flexible longitudinal area consisting of a hollow and flexible torsion cable rigidly connected at the free end thereof to a cannulated bur having sharp profiles.

The transpedicular fusion device according to the present invention comprises a cannulated drill bit comprising, on the opposite side from the cannulated bur, connection means arranged so as to form a link with the cannulated drive system enabling the driving of said cannulated drill bit in back and forth and rotation movements, so as to nibble out gradually and in a controlled manner slots F in said lower endplate Pi and upper endplate Ps of each vertebra Va, Vb, and reduce the nucleic tissues to flaps.

The transpedicular fusion device according to the present invention includes a curved guide pin comprising connection means enabling the holding thereof, the control of the positioning thereof, and the application on the latter of the back and forth movements.

The transpedicular fusion device according to the present invention includes closing devices that consist of pedicular screws enabling the arrangement and the fixation of linking rods of a spinal fixation device.

The transpedicular fusion device according to the present invention includes closing devices that consist of a pedicular screw comprising a linking connector that cooperates with a set screw for the immobilization in translation and rotation of a linking rod.

The present invention also relates to the methods for preparing the intersomatic space, injecting the graft, and placing the closing devices via the transpedicular fusion device.

The method for preparing the intersomatic spaces by an entirely percutaneous transpedicular approach between two vertebrae Va, Vb of a spinal segment of a vertebral column according to the present invention consists:

in carrying out a percutaneous transpedicular sighting for placement and the introduction of straight pedicular cannulas into the pedicles Pa and/or Pb of the vertebrae Va and/or Vb, in introducing into the straight pedicular cannulas a curved guide pin that reaches the vertebral endplates Pi, Ps of the vertebrae Va, Vb, respectively, in slipping a cannulated drill bit connected to a drive system onto the curved pin, in such a manner that the flexible distal end which is rigidly connected to a cannulated bur of said cannulated drill bit perforates by means of back and forth movements the vertebral endplates Pi and Ps at the selected site and the nucleic tissues of the intervertebral disk D in order to produce an intersomatic space Es, in cleaning, by means of a cleaning device introduced into the corresponding straight pedicular cannula, the intersomatic space Es by the injection and the aspiration of saline solution in order to remove a maximum of flaps of nucleic tissues, and in withdrawing the curved pin and the cleaning device from the corresponding straight pedicular cannula.

The method for injecting a graft by an entirely percutaneous transpedicular approach into an intersomatic space Es made between the vertebral endplates Pi, Ps of vertebrae Va, Vb of a spinal segment of a vertebral column according to the present invention consists:

in screwing two closing devices in place of the two straight pedicular cannulas of the lower vertebra Vb, in connecting an injection device that has been filled beforehand with autologous or biological graft into one of the straight pedicular cannulas of the upper vertebra Va, in injecting the graft through one of the straight pedicular cannulas in order to fill the intersomatic space Es and to the point said graft overflows through the other straight pedicular cannula of the upper vertebra Va, in screwing a third closing device in place of the straight pedicular cannula of the upper vertebra Va that does not carry the injection device, in connecting the closing devices located one above the other and rigidly connected to the vertebrae Va, Vb by a first linking device, in continuing the injection of the graft with a pressurization in order to restore the disk height between the vertebrae Va, Vb, in immobilizing in translation and rotation the first linking device in the closing devices, in disconnecting the injection device and in withdrawing the last straight pedicular cannula from the vertebra Va for the fixation of a fourth closing device, and in connecting and in immobilizing the two remaining closing devices by a second linking device.

The method for injecting a graft by an entirely percutaneous transpedicular approach into an intersomatic space Es made between the vertebral endplates Pi, Ps of vertebrae Va, Vb of a spinal segment of a vertebral column according to the present invention consists:

in screwing two closing devices in place of the two straight pedicular cannulas of the upper vertebra Va, in connecting an injection device that has been filled beforehand with autologous or biological graft onto one of the straight pedicular cannulas of the lower vertebra Vb, in injecting the graft through one of the straight pedicular cannulas in order to fill the intersomatic space Es and to the point said graft overflows through the other straight pedicular cannula of the lower vertebra Vb, in screwing a third closing device in place of the straight pedicular cannula of the lower vertebra Vb that does not carry the injection device, in connecting the closing devices located one above the other and rigidly connected to the vertebrae Va, Vb by a first linking device, in continuing the injection of the graft with a pressurization in order to restore the disk height between the vertebrae Va, Vb, in immobilizing in translation and rotation the first linking device in the closing devices, in disconnecting the injection device and in withdrawing the last straight pedicular cannula from the lower vertebra Vb for the fixation of a fourth closing device, and in connecting and in immobilizing the two remaining closing devices by a second linking device.

The method for injecting a graft by an entirely percutaneous transpedicular approach into an intersomatic space Es made between the vertebral endplates Pi, Ps of vertebrae Va, Vb of a spinal segment of a vertebral column according to the present invention consists:

in screwing two closing devices in place of a straight pedicular cannula of the upper vertebra Va and of a straight pedicular cannula of the lower vertebra Vb, in connecting an injection device that has been filled beforehand with autologous or biological graft onto the straight pedicular cannula of the upper vertebra Va, in injecting the graft through the straight pedicular cannula of the upper vertebra Va in order to fill the intersomatic space Es and to the point said graft overflows through the straight pedicular cannula of the lower vertebra Vb, in screwing a third closing device in place of the straight pedicular cannula of the lower vertebra Vb, in connecting the closing devices located one above the other and rigidly connected to the vertebrae Va, Vb by a first linking device, in continuing the injection of the graft with a pressurization in order to restore the disk height between the vertebrae Va, Vb, in immobilizing in translation and rotation the first linking device in the closing devices, in disconnecting the injection device and in withdrawing the last straight pedicular cannula from the lower vertebra Va for the fixation of a fourth closing device, and in connecting and in immobilizing the two remaining closing devices by a second linking device.

The method for injecting a graft by an entirely percutaneous transpedicular approach into an intersomatic space Es made between the vertebral endplates Pi, Ps of vertebrae Va, Vb of a spinal segment of a vertebral column according to the present invention consists:

in screwing two closing devices in place of a straight pedicular cannula of the upper vertebra Va and of a straight pedicular cannula of the lower vertebra Vb, in connecting an injection device that has been filled beforehand with autologous or biological graft onto the straight pedicular cannula of the lower vertebra Vb, in injecting the graft through the straight pedicular cannula of the lower vertebra Vb in order to fill the intersomatic space Es and to the point said graft overflows through the straight pedicular cannula of the upper vertebra Va, in screwing a third closing device in place of the straight pedicular cannula of the upper vertebra Va, in connecting the closing devices located one above the other and rigidly connected to the vertebrae Va, Vb by a first linking device, in continuing the injection of the graft with a pressurization in order to restore the disk height between the vertebrae Va, Vb, in immobilizing in translation and rotation the first linking device in the closing devices, in disconnecting the injection device and in withdrawing the last straight pedicular cannula from the lower vertebra Vb for the fixation of a fourth closing device, and in connecting and in immobilizing the two remaining closing devices by a second linking device. The method for injecting a graft by an entirely percutaneous transpedicular approach into an intersomatic space Es made between the endplates Pi, Ps of vertebrae Va, Vb of a spinal segment of a vertebral column according to the present invention consists:

in screwing two closing devices into the pedicles Pb of the lower vertebra Vb, in connecting an injection device that has been filled beforehand with autologous or biological graft onto a straight pedicular cannula of the upper vertebra Va, in injecting the graft through one of the straight pedicular cannulas of the upper vertebra Va in order to fill the intersomatic space Es and to the point said graft overflows through the other straight pedicular cannula of the upper vertebra Va, in screwing a third closing device in place of the straight pedicular cannula of the upper vertebra Va that does not carry the injection device, in connecting the closing devices located one above the other and rigidly connected to the vertebrae Va, Vb by a first linking device, in continuing the injection of the graft with a pressurization in order to restore the disk height between the vertebrae Va, Vb, in immobilizing in translation and rotation the first linking device in the closing devices, in disconnecting the injection device and in withdrawing the last straight pedicular cannula from the upper vertebra Va for the fixation of a fourth closing device, and in connecting and in immobilizing the two remaining closing devices by a second linking device.

The method for injecting a graft by an entirely percutaneous transpedicular approach into an intersomatic space Es made between the endplates Pi, Ps of vertebrae Va, Vb of a spinal segment of a vertebral column according to the present invention consists:

in screwing two closing devices in the pedicles Pa of the upper vertebra Va, in connecting an injection device that has been filled beforehand with autologous or biological graft onto a straight pedicular cannula of the lower vertebra Vb, in injecting the graft through one of the straight pedicular cannulas of the lower vertebra Vb in order to fill the intersomatic space Es and to the point said graft overflows through the other straight pedicular cannula of the lower vertebra Vb, in screwing a third closing device in place of the straight pedicular cannula of the lower vertebra Vb that does not carry the injection device, in connecting the closing devices located one above the other and rigidly connected to the vertebrae Va, Vb by a first linking device, in continuing the injection of the graft with a pressurization in order to restore the disk height between the vertebrae Va, Vb, in disconnecting the injection device and in withdrawing the last straight pedicular cannula from the lower vertebra Vb for the fixation of a fourth closing device, and in connecting and in immobilizing the two remaining closing devices by a second linking device.

The method for placing a closing device by an entirely percutaneous transpedicular approach in the vertebrae Va, Vb of a spinal segment of a vertebral column according to the present invention consists:

in introducing a secure pin device through one of the straight pedicular cannulas already in place up to the anterior wall of the corresponding vertebra Va, Vb, in deploying the forked portion of the secure pin so that the latter is supported in the spongy bone of the vertebra Va, Vb, in withdrawing the corresponding straight pedicular cannula from the vertebra Va, Vb, in screwing a pedicular screw of the closing device into the body of the vertebra Va, Vb using the guidance of the secure pin, in withdrawing the secure pin through the cannulated pedicular screw before the end of the screwing of the latter to the desired depth.

The following description regarding the appended drawings given as non-limiting examples will make it possible to better understand the invention, the features thereof, and the advantages that it is capable of procuring.

Figure 1:
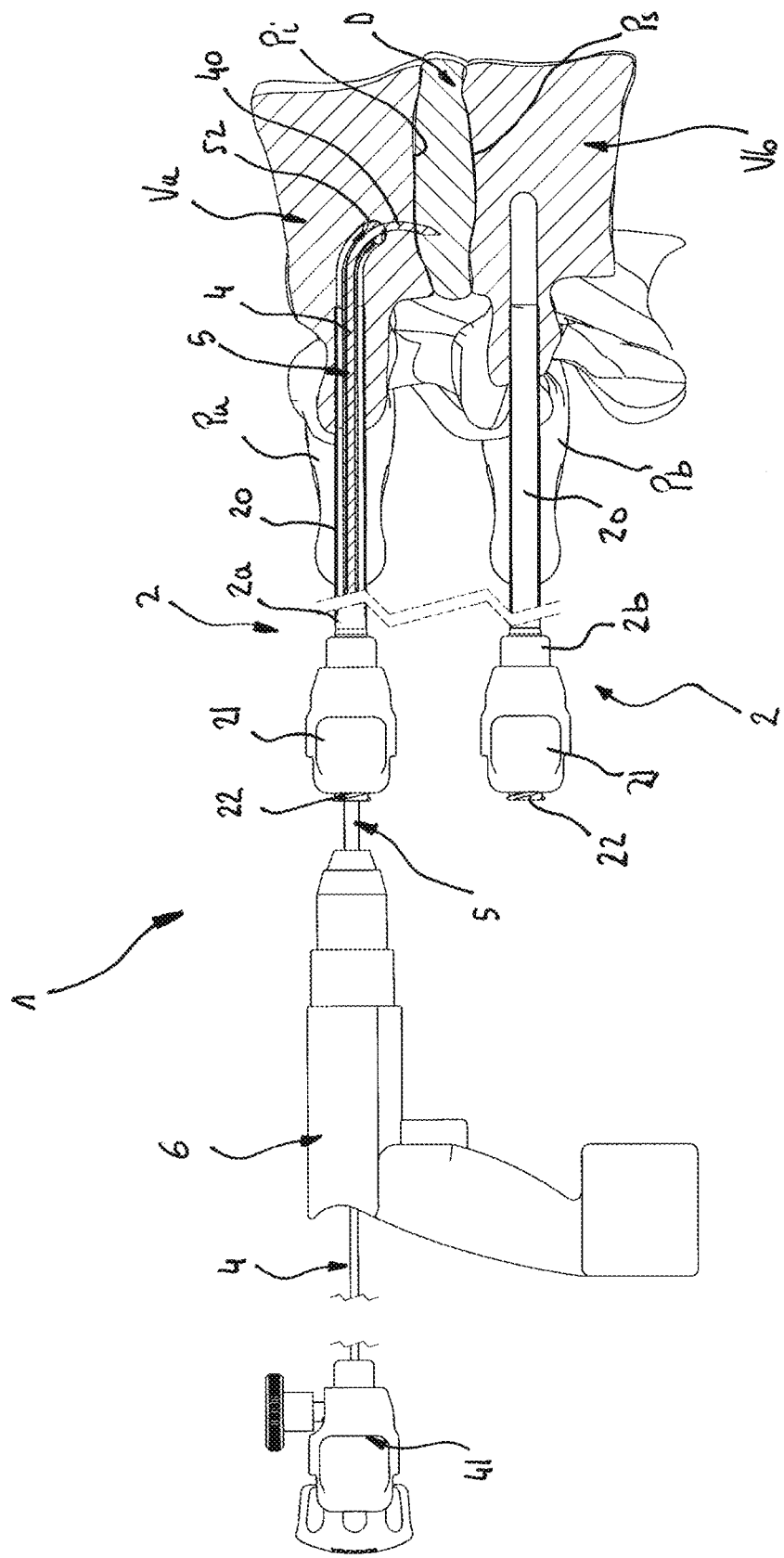
FIGS. 1 to 4 are profile views illustrating a spinal segment of a vertebral column in which an intersomatic space is arranged by means of a transpedicular fusion device according to the present invention.
Figure 2:
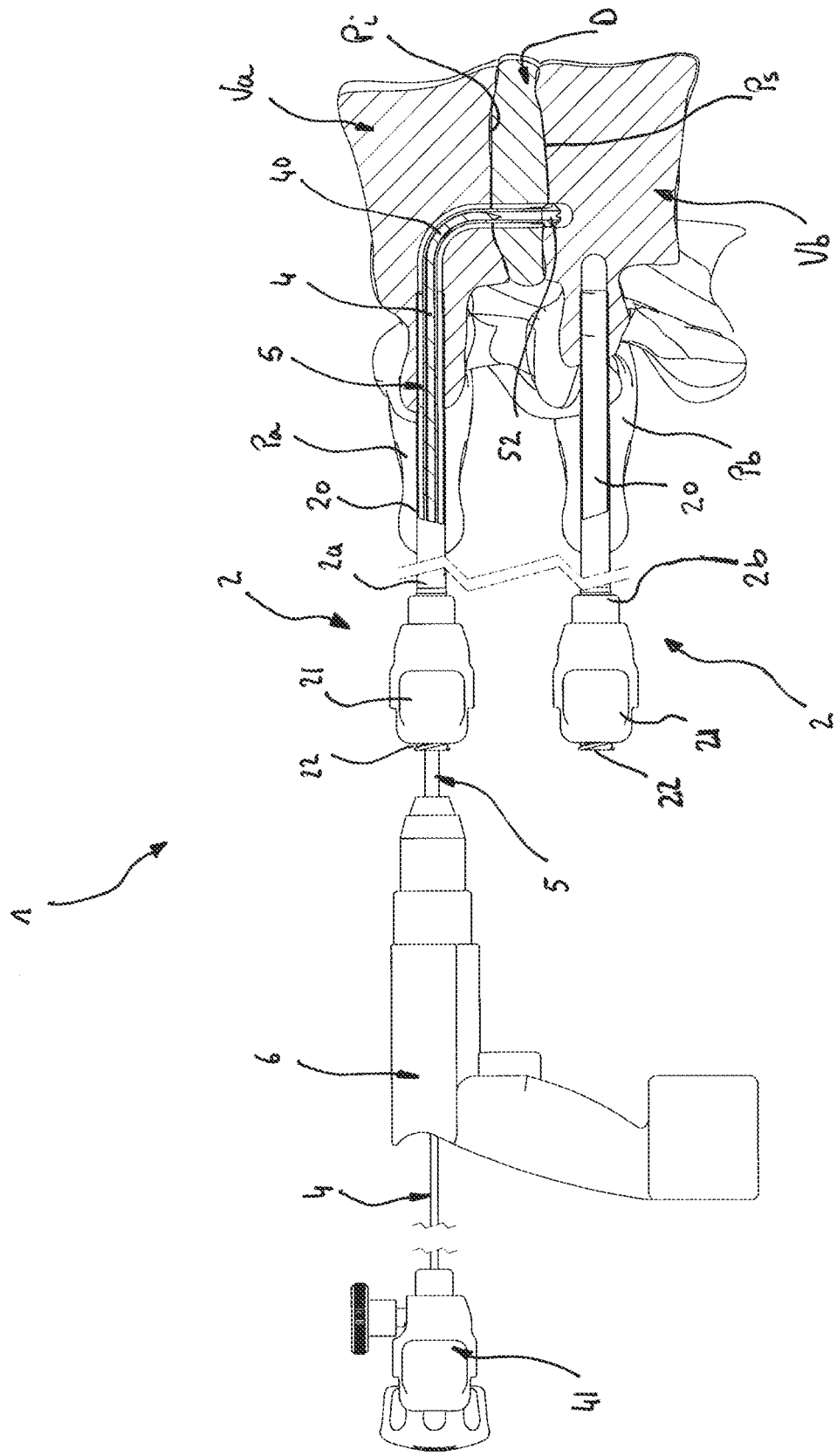

In FIGS. 1 to 5, a fusion device 1 according to the present invention is represented, including two straight pedicular cannulas 2, 3 per vertebra Va, Vb, used as secure work channel and sighting positioner.

Thus, for the vertebra Va, a straight pedicular cannula 2a and 3a will be screwed into each pedicle Pa, while, for the vertebra Vb, a straight pedicular cannula 2b and 3b will be screwed into each pedicle Pb. During the transpedicular sighting operations, the straight pedicular cannulas 2a, 2b and/or 3a, 3b make it possible to guide the different instruments in the direction of the vertebral endplates and to the predetermined site.

Each pedicular cannula 2, 3 consists of a tube 20, 30 rigidly connected at one of the ends thereof to a gripping head 21, 31. The gripping head 21, 31 comprises in its middle a connection means 22, 32 enabling instrument immobilization.

The fusion device 1 includes at least one resiliently deformable guide pin 4 having, in deformed position, an end with pointed curved profile 40 ensuring the implantation thereof in the upper and/or lower endplate of the corresponding vertebra Va, Vb. On the opposite side from the curved profile 40, the guide pin 4 cooperates with a gripping system 41 allowing the surgeon to move said pin.

Figure 6:
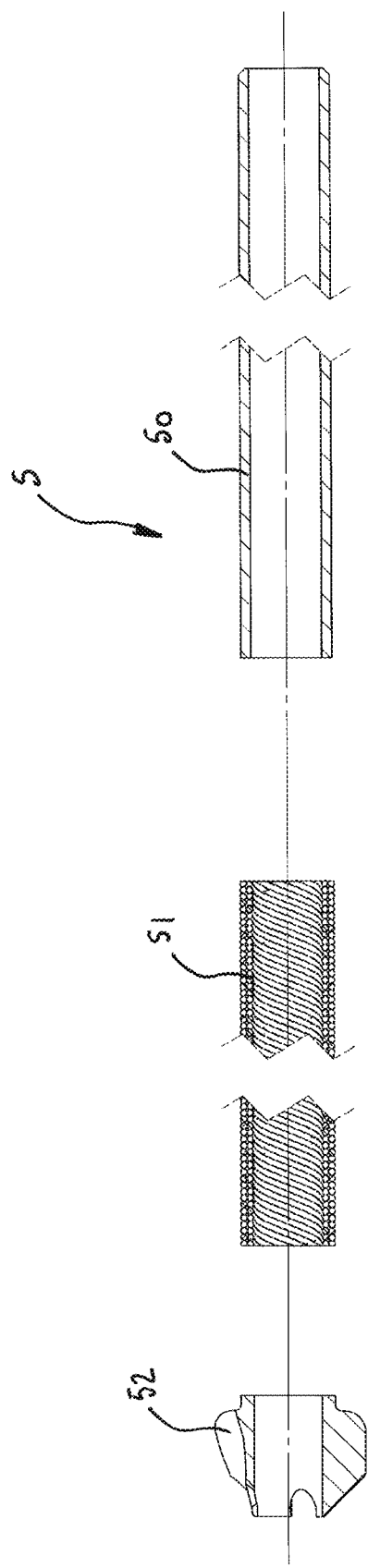
FIG. 6 is a view showing the flexible cannulated drill bit of the transpedicular fusion device according to the present invention.

The fusion device 1 comprises a cannulated drive system 6 on which a flexible cannulated drill bit 5 is mounted, which includes a rigid cannulated rod 50 extended by a flexible longitudinal area consisting, for example, of a hollow and flexible torsion cable 51 rigidly connected at its free end to a cannulated bur 52 having sharpened profiles (FIG. 6).

The cannulated drive system 6 makes it possible to drive said cannulated drill bit 5 in back and forth and in rotation movements, so that the cannulated bur 52 nibbles out gradually and in a controlled manner slots in said upper and lower endplates of each vertebra Va, Vb and reduces the nucleic tissues of the intervertebral disk D to flaps.

Figure 7:
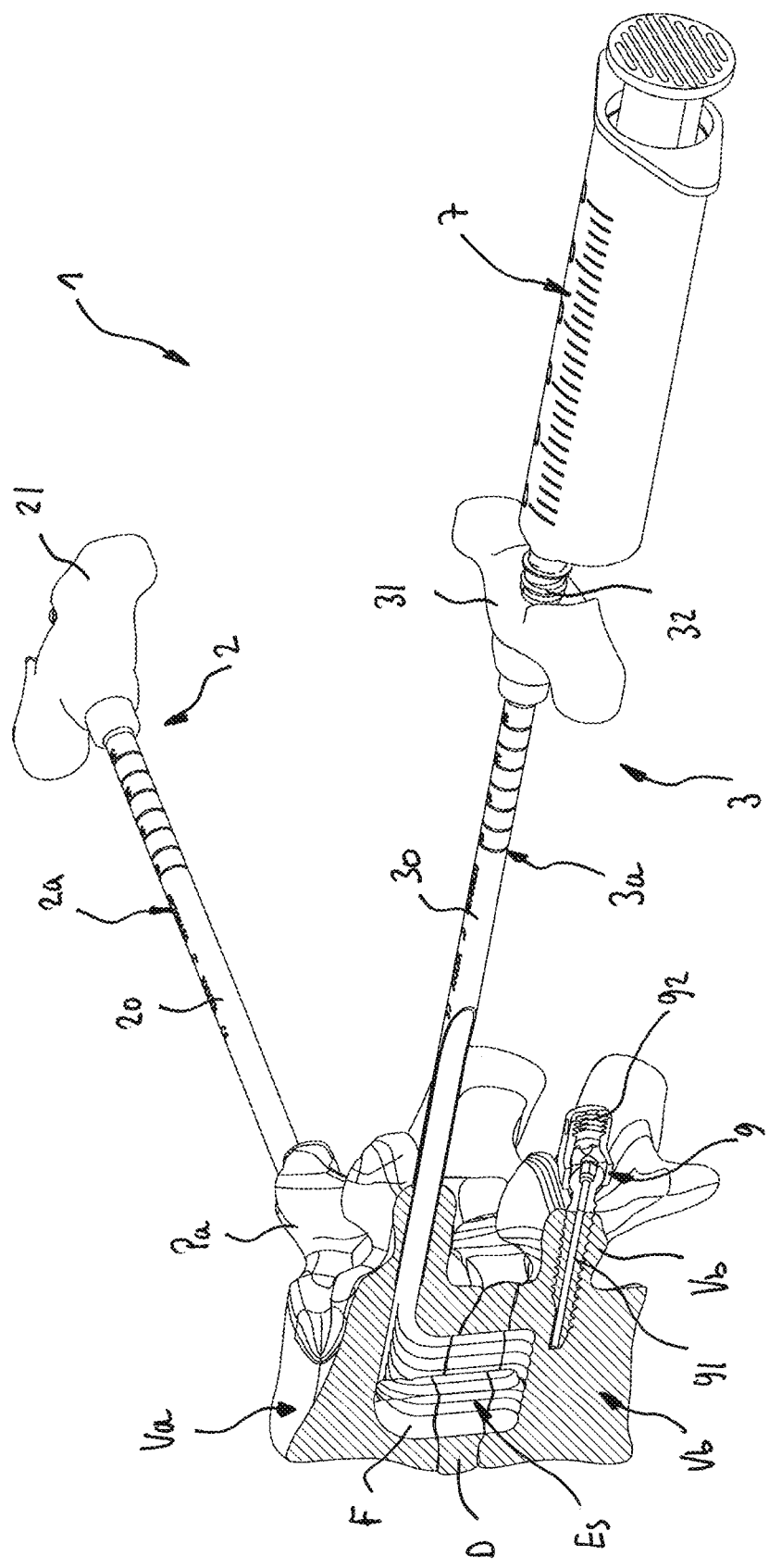
FIG. 7 is a perspective view representing a spinal segment of a vertebral column, cut along a vertical axis making it possible to show the profile of the intersomatic space produced before the introduction of the autologous or biological graft by means of the transpedicular fusion device according to the present invention.

In FIG. 7, the fusion device 1 comprising an injection device 7 is represented, said injection device being connected to one of the pedicular cannulas 2a, 2b and 3a, 3b remaining in the operation site for the injection of a graft 8 into the intersomatic space thus produced.

The fusion device 1 comprises closing devices 9 that are screwed into the holes left free after the retraction of the straight pedicular cannulas 2a, 2b and 3a, 3b.

In our embodiment example, the closing devices 9 consist of pedicular screws 90 connected by linking rods 91 forming a spinal fixation device which is known per se.

The drive system 6 on which the flexible cannulated drill bit 5 is mounted comprises guide means making it possible to leave a free passage for the curved guide pin 4.

After the percutaneous transpedicular sighting has been carried out by the surgeon, the latter prepares the intersomatic operation site by means of the fusion device 1 according to the present invention, by producing, using different tools and a precise operating procedure, slots F in the lower vertebral endplate Pi for the upper vertebra Va and upper Ps for the lower vertebra Vb. These tools also enable a reduction to flaps of the nucleic tissues of the intervertebral disk D, said intervertebral disk being located between the overlying vertebra Va and the underlying vertebra Vb (FIGS. 1 to 5).

The straight pedicular cannulas 2a, 2b and 3a, 3b are screwed into the corresponding pedicle Pa, Pb, respectively, so that the curved pin 4 can reach the lower endplate Pi and upper endplate Ps at the site determined by the position of said straight pedicular cannulas 2a, 2b and 3a, 3b and perforate said vertebral plates Pi and Ps by impaction.

After having unscrewed the corresponding straight pedicular cannulas 2a, 2b and 3a, 3b up to the edge of the posterior wall of the vertebra Va, Vb and in a manner so as to prevent any injury to neurological elements, the cannulated drill bit 5 which is flexible at its distal end is slipped onto the curved pin 4 which will be used as guide.

The flexible cannulated drill bit 5 is connected to the drive system 6 which includes a motor ensuring the driving in rotation of said drill bit for the production of the slots F.

The surgeon produces the first perforation or slot F of the endplates Pi, Ps and of the intervertebral disk D by moving the flexible cannulated drill bit 5 around the curved guide pin 4.

The next slots F are produced by a progressive nibbling out of the endplates Pi, Ps and of the intervertebral disk D.

For this purpose and after the first perforation, the surgeon moves back the drive system 6 rigidly connected to the flexible cannulated drill bit 5 in order to free the curved portion of the guide pin 4.

Then, the guide pin 4 is moved so that it is applied against the internal wall of the first perforation.

When the guide pin 4 is in place, the drive system 6 is moved back so that the flexible cannulated drill bit 5 broadens the first perforation by nibbling out the endplates Pi, Ps and the intervertebral disk D in order to produce a second slot F.

Figure 3:
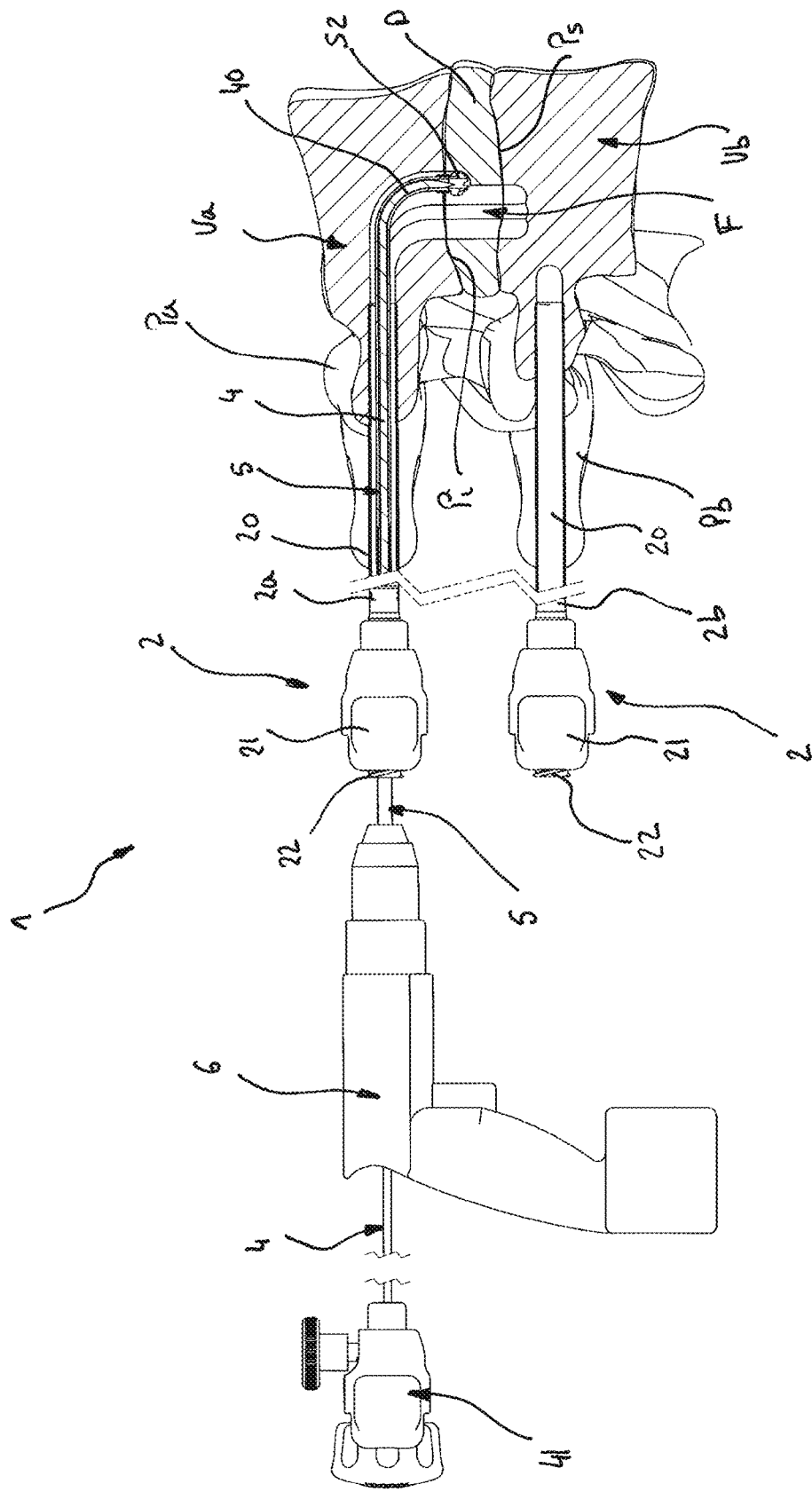
Figure 4:
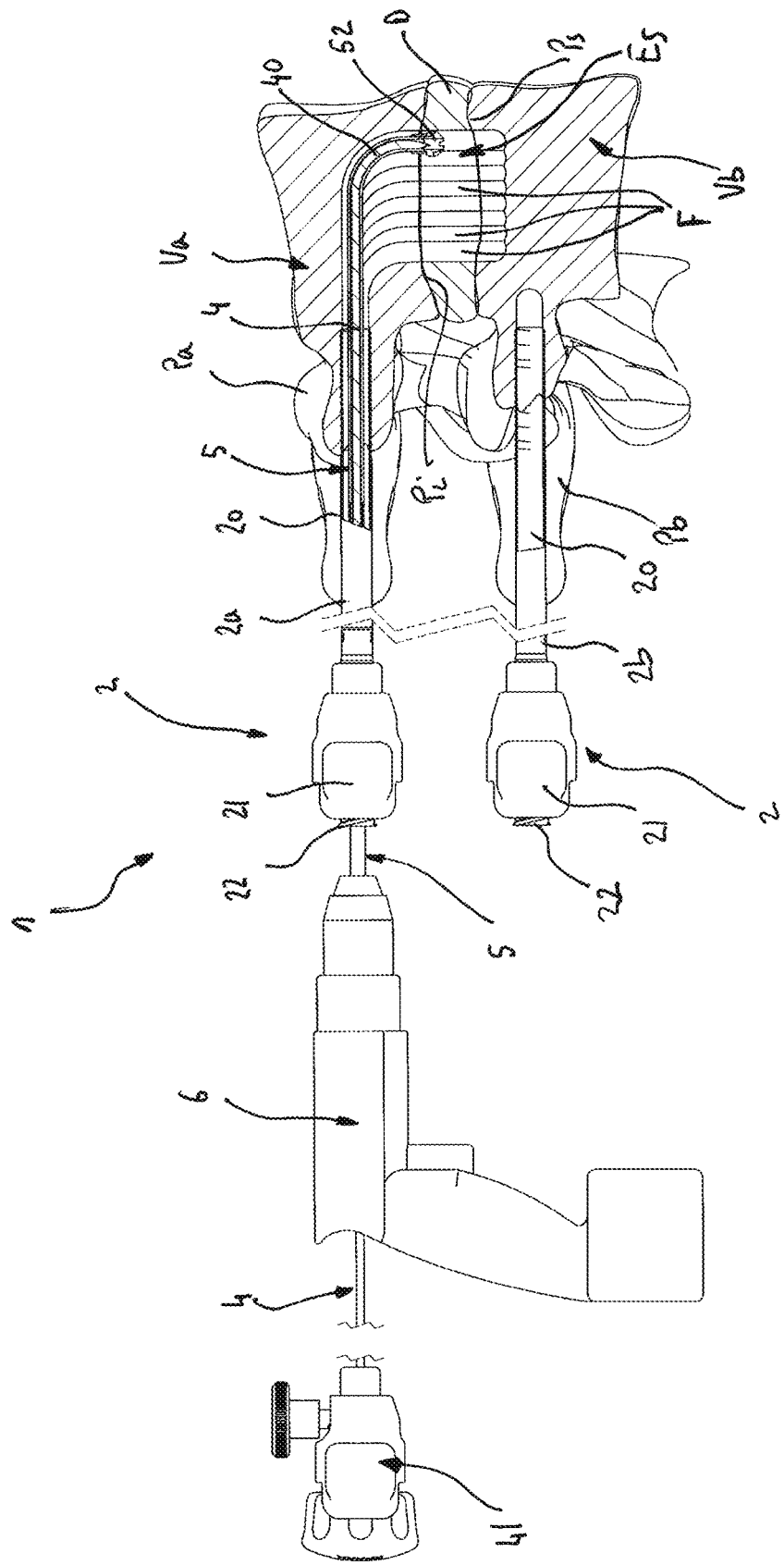
Figure 5:
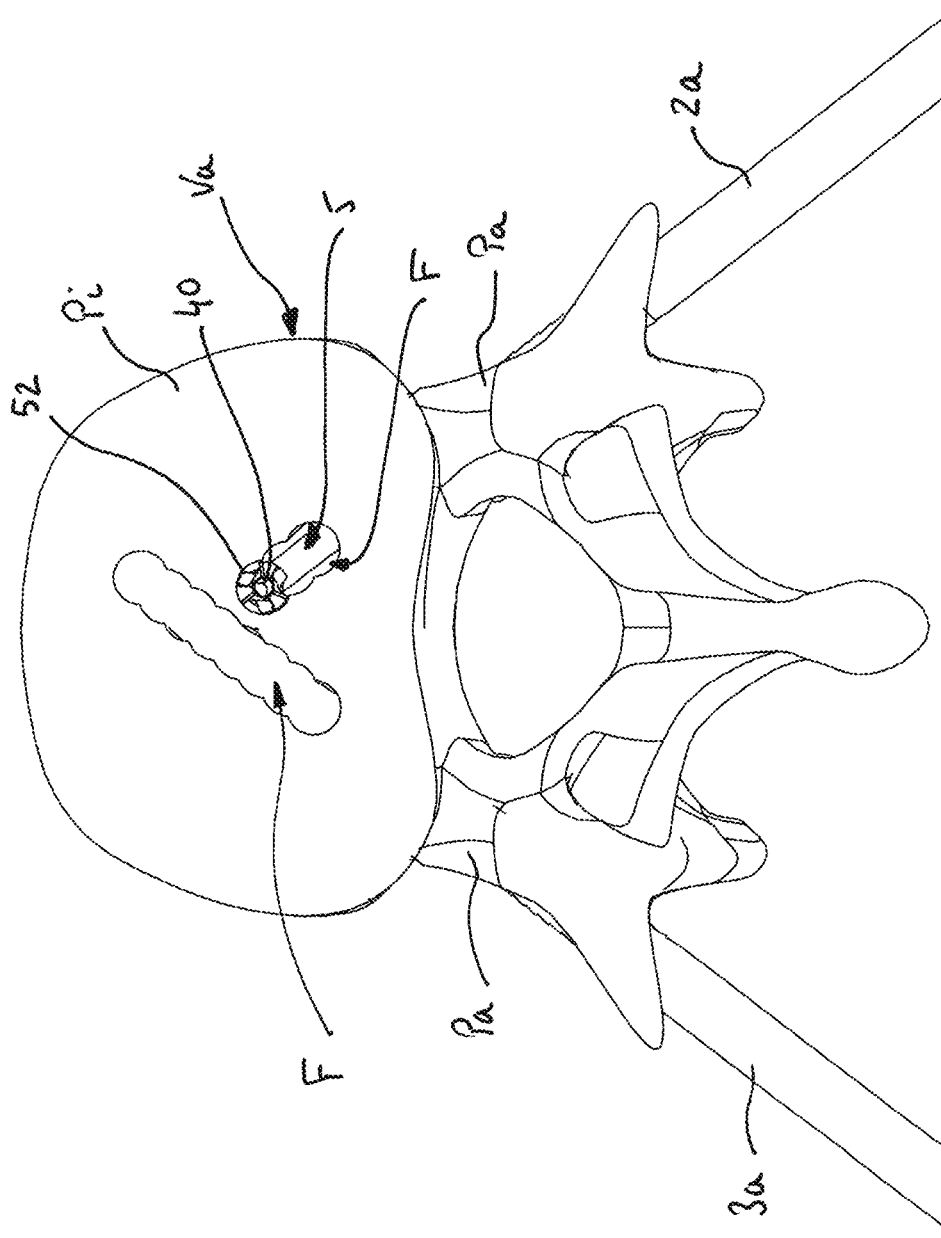
FIG. 5 is a view from below in the coronal plane of the intervertebral disk D, illustrating the lower endplate of the upper vertebra of the spinal segment nibbled out by means of the flexible cannulated drill bit of the transpedicular fusion device according to the present invention.

For this purpose, the surgeon moves the drive system 6 in back and forth movements around the guide pin 4 as many times as necessary, so that the flexible cannulated drill bit 5 produces all the slots F by nibbling out the corresponding vertebral endplates Pi, Ps (FIGS. 3 to 5).

The result obtained by the repetition of these operations makes it possible to produce a set of slots F enabling the production of an intra-nucleic space Es having a large opening, between the overlying vertebra Va and underlying vertebra Vb (FIG. 4).

These operations for hollowing out each one of these slots F in the vertebral endplates Pi, Ps are carried out through the straight pedicular cannulas 2a, 3a and/or 2b, 3b which are rigidly connected respectively to the pedicles Pa, Pb of the adjacent vertebrae Va, Vb in the same manner as above.

These operations are carried out by means of the flexible cannulated bur 52 guided by the curved pin 4 introduced respectively into the straight pedicular cannulas 2a, 2b and/or 3a, 3b which were screwed beforehand into the pedicles Pa and Pb during transpedicular sighting operations, in order to perforate the vertebral endplate Pi and Ps at the chosen site.

Then, the surgeon proceeds using the straight pedicular cannulas 2a, 3a and/or 2b, 3b to a cleaning of the grafting operation site by the injection and the aspiration of saline solution in order to remove a maximum of flaps of nucleic tissues. For example, the cleaning of the grafting operation site can be carried out by the introduction of a flexible tube through the cannulas leading into the intra-nucleic space Es in order to prevent any contact of the saline solution with the spongy bone of the vertebrae Va, Vb (FIG. 8).

Figure 8:
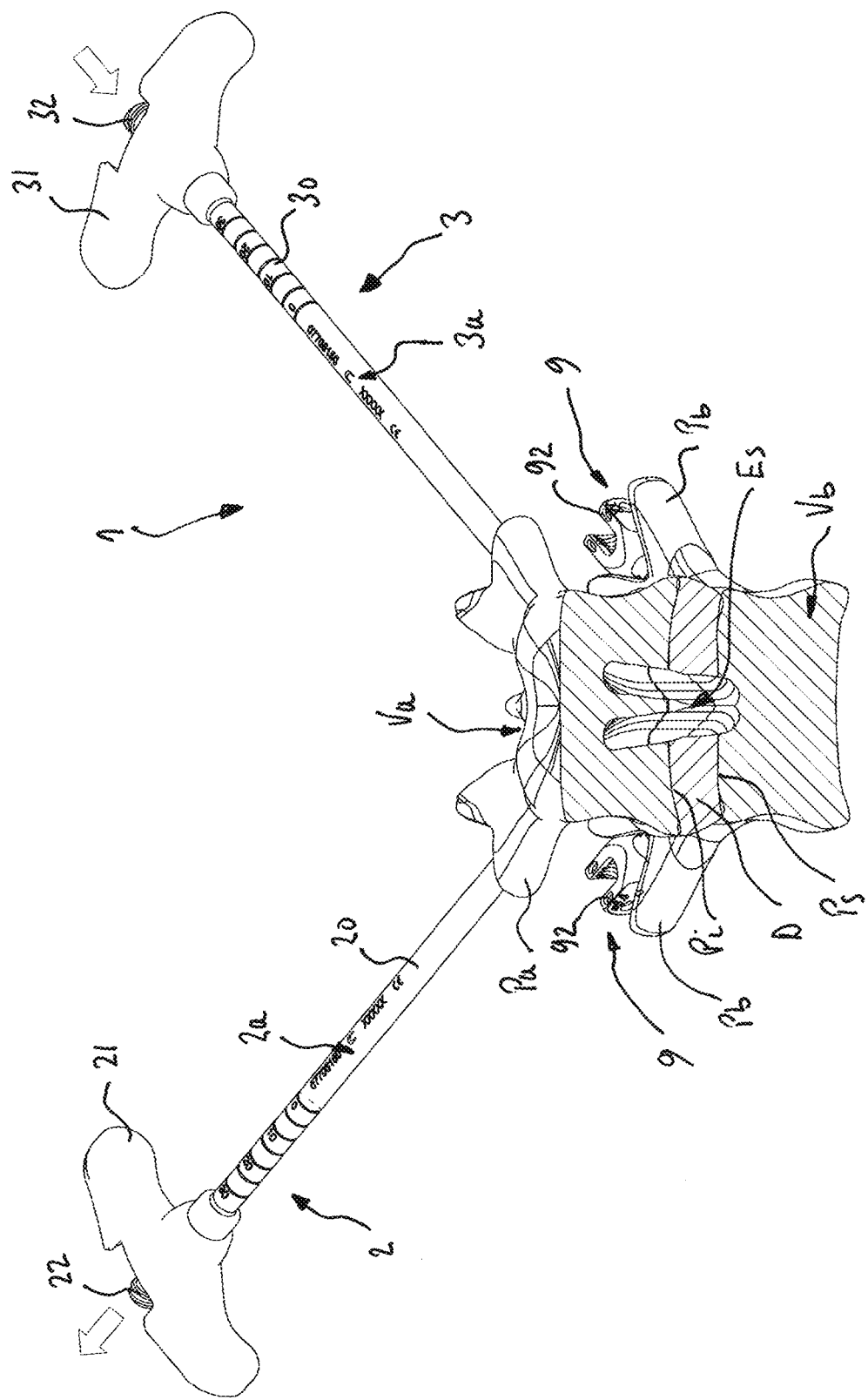
FIG. 8 is a perspective view illustrating a spinal segment of a vertebral column, cut along a vertical axis making it possible to show in a front view the intersomatic space produced before the introduction of the autologous or biological graft by means of the transpedicular fusion device according to the present invention.

Before the injection of the graft, the surgeon screws closing devices 9, such as, for example, polyaxial pedicular screws 90, into the pedicles Pb of the lower vertebra Vb (FIGS. 7 and 8).

Figure 23:
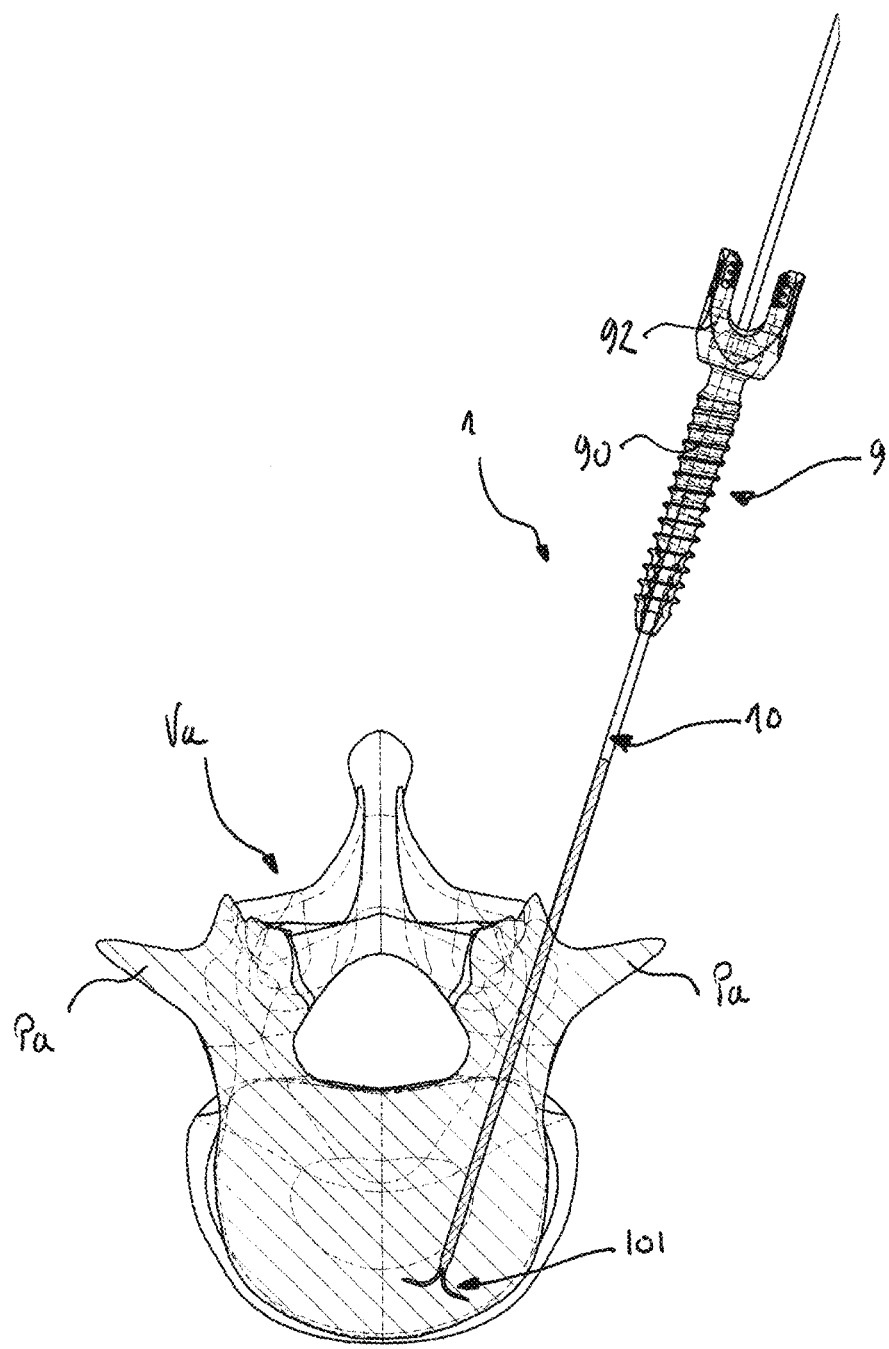
FIG. 23 is a view representing an example of a closing device implanted in the pedicles of the vertebrae of the spinal segment by means of the transpedicular fusion device according to the present invention.

The placement of closing devices 9 in the vertebra Vb is carried out as illustrated in FIG. 23 and according to the following procedure:

introduction of a secure pin device 10 through one of the straight cannulas 2b, 3b already in place, up to the anterior wall;

deployment of the forked portion 102 of the secure pin 101, so that the latter is supported in the spongy bone of the vertebra Vb;

retraction of the corresponding straight cannula 2b, 3b from the vertebra Vb;

screwing of the first pedicular screw 90 of the closing device 9 in the body of the vertebra Vb using the guidance of the secure pin 101;

retraction of the secure pin 101 through the cannulated pedicular screw 90 before the end of the screwing in of the latter, additional screwing in of the pedicular screw 90 to the desired depth.

These operations are repeated for the placement of the second pedicular screw 90 forming the closing device 9 in the lower vertebra Vb.

Figure 9:
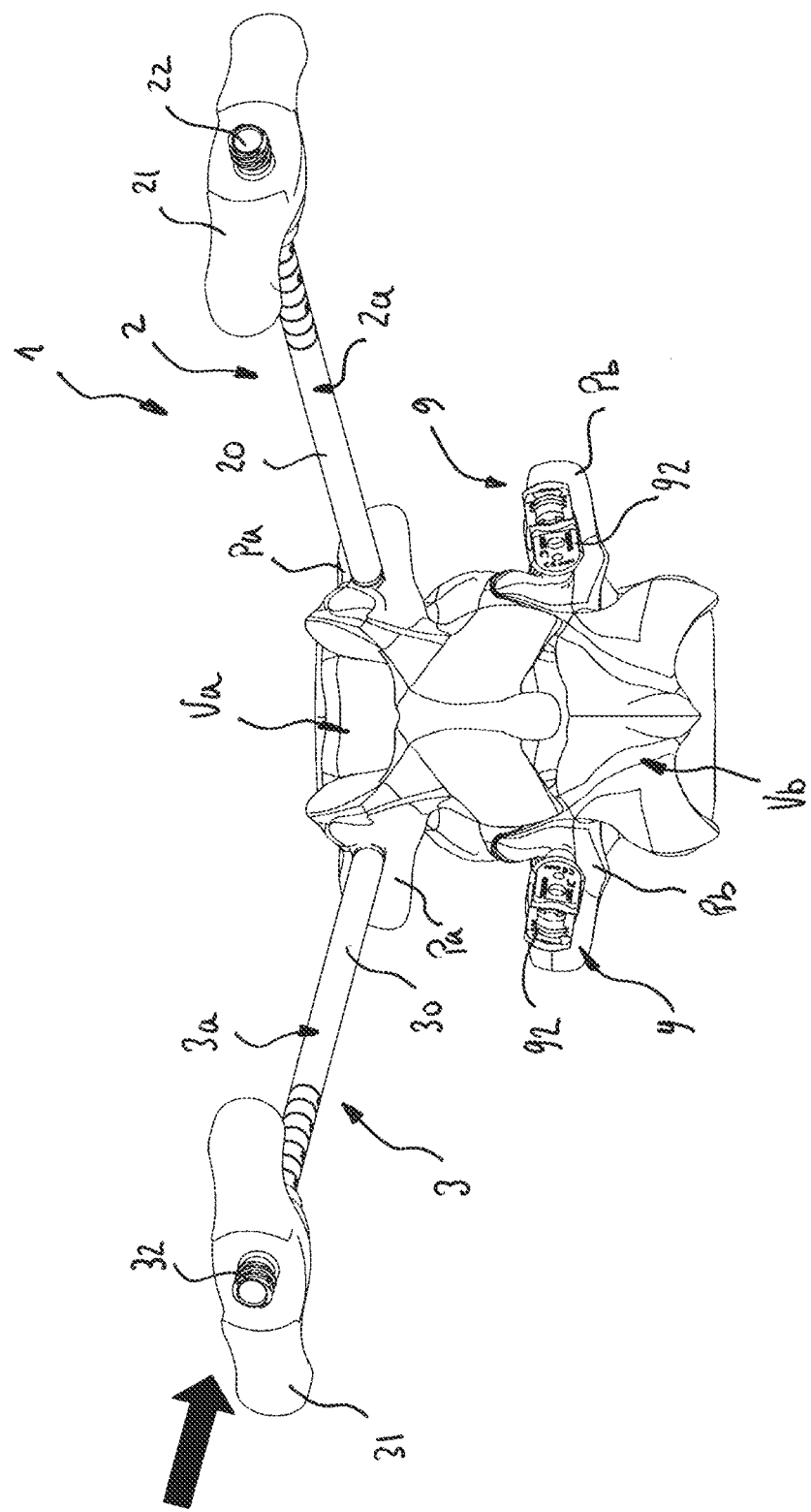
FIGS. 9 to 12 are views representing the different steps of preparation, of injection of the autologous or biological graft into the intersomatic space, and of stabilization of a spinal segment by means of the transpedicular fusion device according to the present invention.

The introduction of the autologous or biological graft 8 is carried out by means of the injection device 7 which the surgeon connects to one of the straight cannulas 2a, 3a implanted in the upper vertebra Va (FIGS. 7 and 9).

The autologous graft 8 can be harvested from the iliac crest and prepared with specific instruments in order to obtain a slurry whose grain size is compatible with the injection through, on the one hand, the injection device 7 and, on the other hand, the corresponding straight cannula 2a, 3a.

In the case of biological graft 8, the product is prepared from different components whose grain size matrix is compatible with an injection through, on the one hand, the injection device 7 and, on the other hand, the corresponding straight cannula 2a, 3a.

The surgeon carries out the injection of the graft 8 through the straight cannula 3a, for example, which is connected beforehand to the injection device 7, until one can see the flow of the product constituting the graft 8 through the other straight cannula 2a in order to verify that the intra-nucleic space Es is perfectly filled.

Figure 10:
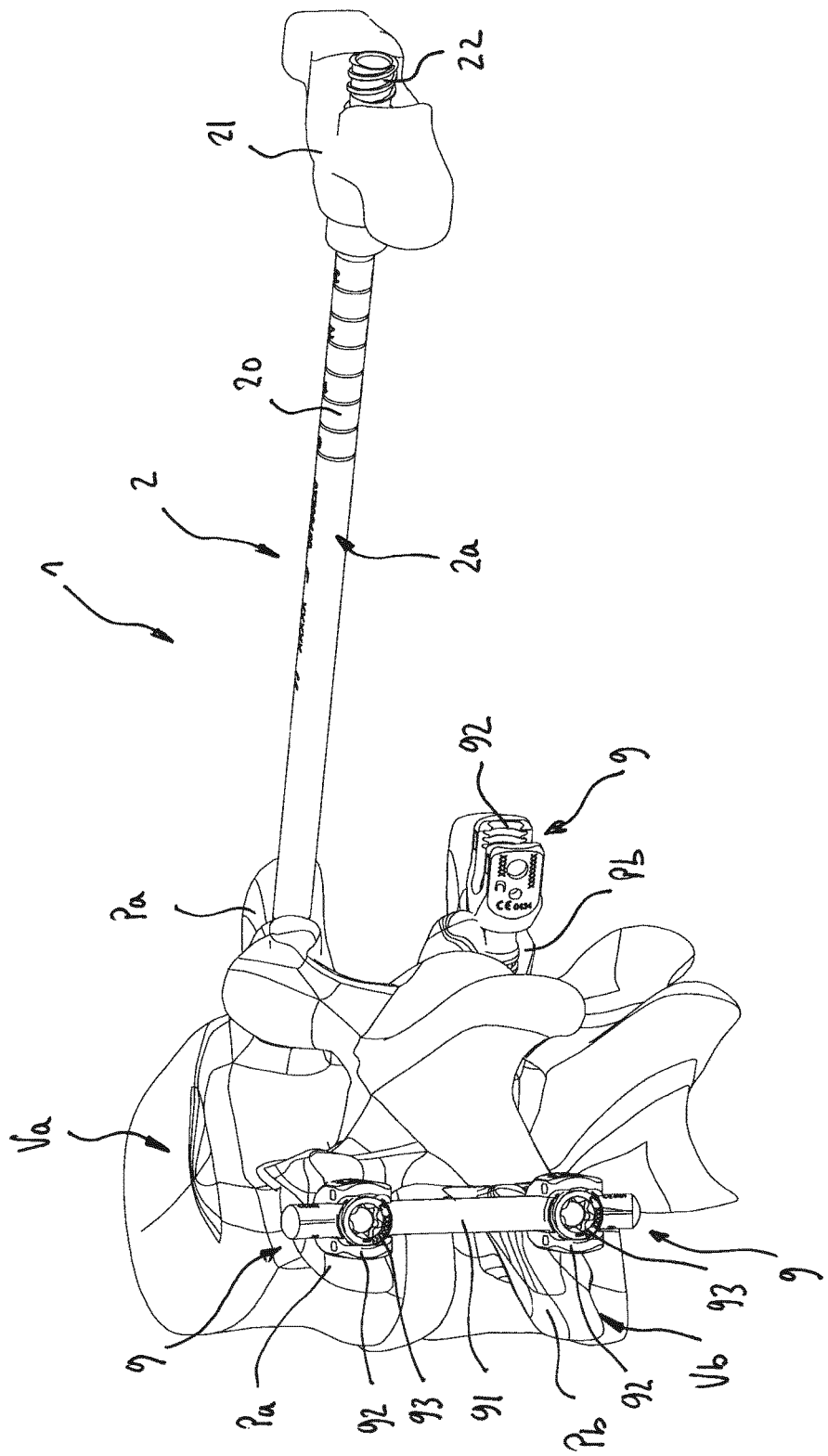

The surgeon proceeds to the fixation of a third closing device 9 consisting of a pedicular screw 90 which is screwed into the pedicle of the vertebra Va by means of the straight cannula 3a and according to the same procedure as described above for the placement of the pedicular screws 90 in the lower vertebra Vb (FIG. 10).

Then, the surgeon introduces a first linking rod 91 connecting the pedicular screws 90 located one above another and rigidly connected to the vertebrae Va and Vb. The first linking rod 91 is immobilized in connectors 92 rigidly connected to each pedicular screw 90 by set screws 93. This immobilization is limited, in a first phase, in order to guarantee freedom of translation of the linking rod 91 between the pedicular screws 90 (FIGS. 10 and 12).

The surgeon continues the injection of the graft 8 by means of the injection device 7 connected to the remaining straight cannula 2a or 3a with a pressurization in order to restore the disk height between the vertebrae Va and Vb of the spinal segment. The pressure applied during the injection of the graft 8 between the vertebrae Va and Vb makes it possible to put the annulus under tension again.

Figure 12:
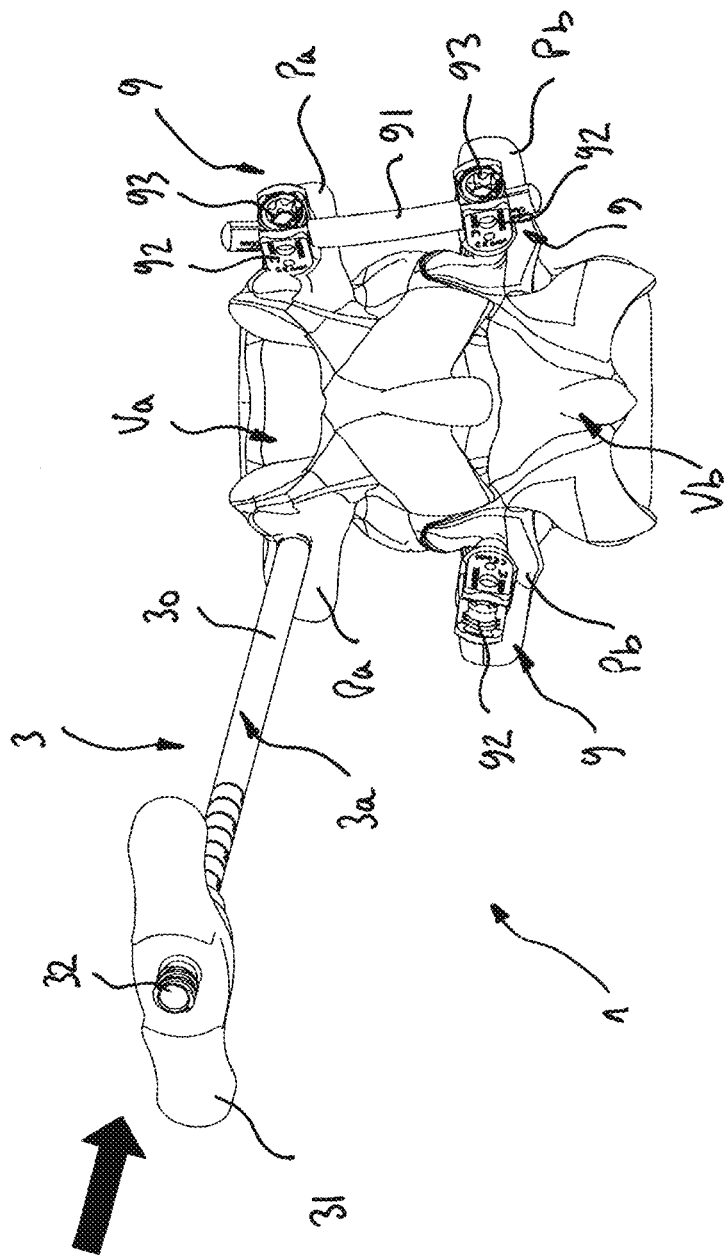

This operation is carried out under radiographic control in the operating unit and stopped when the disk height appears to be satisfactory (FIGS. 10 and 12).

As soon as the disk height between the vertebrae Va and Vb appears to be satisfactory, the surgeon definitively immobilizes the first linking rod 91 in the connectors 92 of the pedicular screws 90 by an additional tightening of the set screws 93.

The injection device 7 is disconnected from the straight cannula 2a, and the surgeon proceeds to the placement of a fourth and last closing device 9 consisting of a pedicular screw 90 which is screwed into the pedicle of the vertebra Va by means of said straight cannula 2a and according to the same procedure as the one described above for the placement of the pedicular screws 90 in the lower vertebra Vb.

Figure 11:
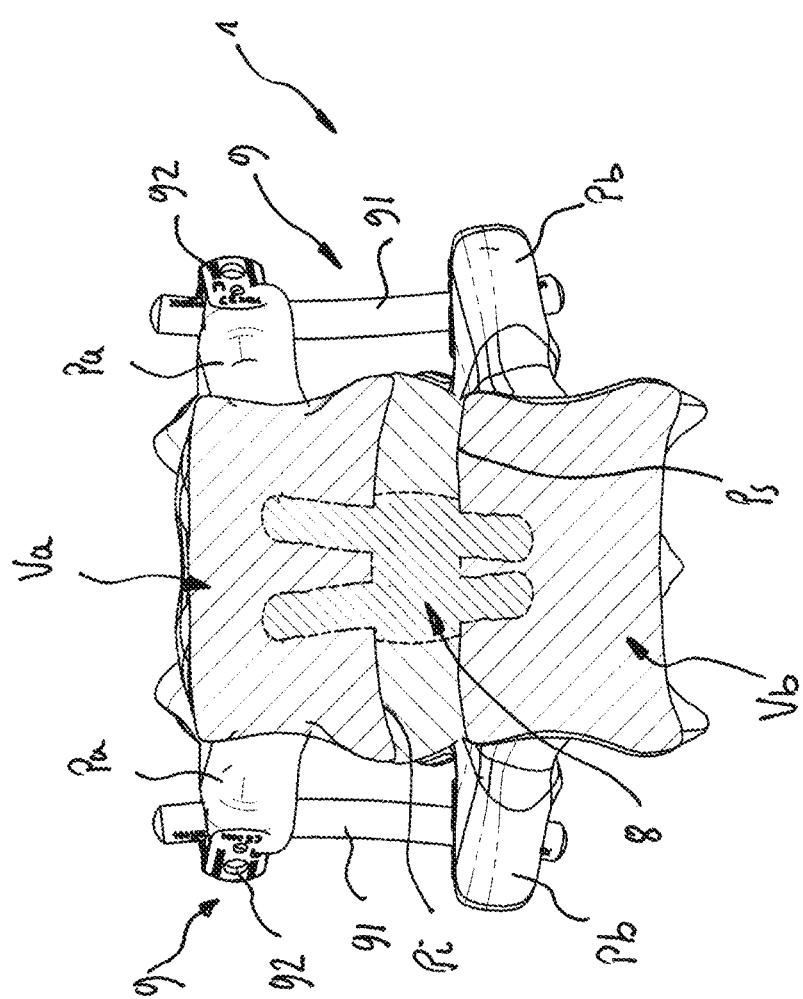

Then, the surgeon introduces a second linking rod 91 connecting the other pedicular screws 90 located one above the other and rigidly connected to the vertebrae Va and Vb. The second linking rod 91 is immobilized in connectors 92 rigidly connected to each pedicular screw 90 by set screws 93 (FIG. 11).

At this stage, the surgeon can adjust the desired lordosis by compression maneuvers performed by means of a specific instrument and definitively immobilize the linking rods 91 in the pedicular screws 90.

The closing of the four percutaneous incisions is carried out in the usual manner.

The graft which has been compacted as a result of the injection thereof under a certain pressure into the space for receiving the graft acts as an intervertebral prop. Indeed, the graft that is maintained compact in the casing consisting of the annulus and of the vertebral bodies ensures an effective and dynamic hold that promotes fusion.

In addition, the vascularization of the graft site due to the perforation of the vertebral endplates Pi, Ps makes it possible to obtain highly favorable conditions (neutral pH, and supplies of nutrients and of bioactive compounds) for a rapid and quality fusion. The dynamic stressing and the abundant vascularization of the graft make it possible to consistently reduce the fusion failure rate.

FIGS. 13 to 22 represent different possibilities of injection of the autologous or biological graft 8 by an entirely percutaneous transpedicular approach into the intersomatic space Es made between the vertebral endplates Pi, Ps of the vertebrae Va, Vb of the spinal segment by means of the transpedicular fusion device 1.

Figure 13:
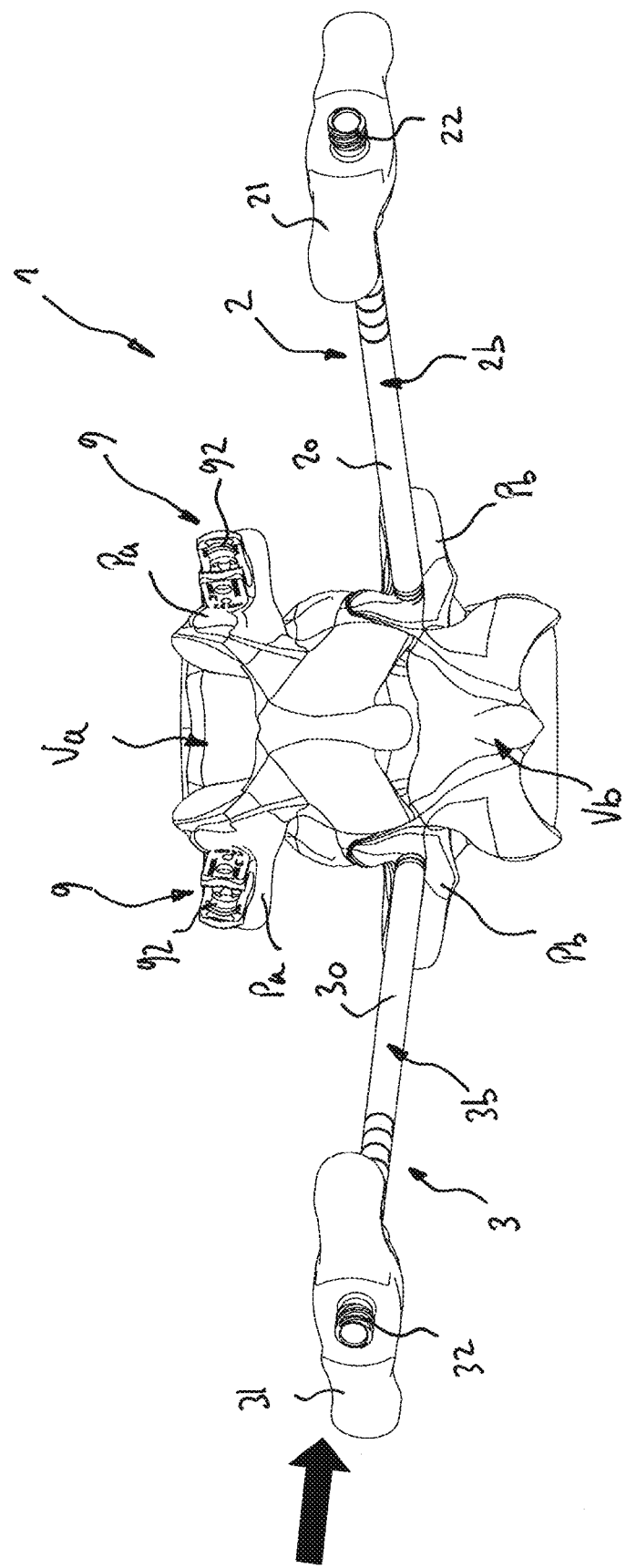
FIGS. 13 to 22 are views illustrating variants of the different steps of preparation, of injection of the autologous or biological graft into the intersomatic space, and of stabilization of a spinal segment by means of the transpedicular fusion device according to the present invention.
Figure 14:
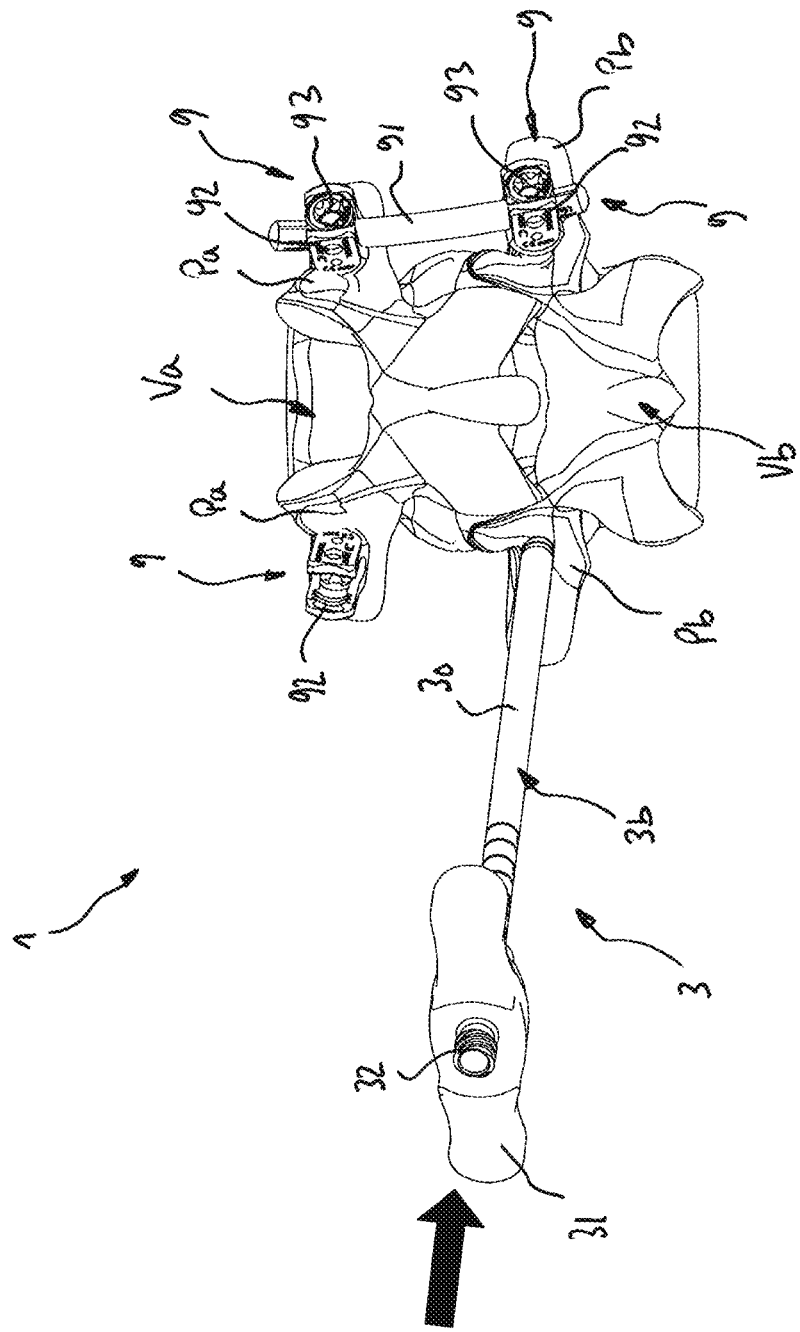

FIGS. 13 and 14 show the following steps of injection of the autologous or biological graft 8:

in screwing two closing devices 9 in place of the two straight pedicular cannulas 2a, 3a of the upper vertebra Va, in connecting an injection device 7 that has been filled beforehand with autologous or biological graft 8 onto one of the straight pedicular cannulas 2b, 3b of the lower vertebra Vb, in injecting the graft 8 through one of the straight pedicular cannulas 2b, 3b in order to fill the intersomatic space Es and to the point said graft overflows through the other straight pedicular cannula of the lower vertebra Vb, in screwing a third closing device 9 in place of the straight pedicular cannula of the lower vertebra Vb that does not carry the injection device 7, in connecting the closing devices 9 located one above the other and rigidly connected to the vertebrae Va, Vb by a first linking device, in continuing the injection of the graft 8 with a pressurization in order to restore the disk height between the vertebrae Va, Vb, in immobilizing in translation and rotation the first linking device in the closing devices 9, in disconnecting the injection device 7 and in withdrawing the last straight pedicular cannula from the lower vertebra Vb for the fixation of a fourth closing device 9, and in connecting and in immobilizing the two remaining closing devices 9 by a second linking device.

Figure 15:
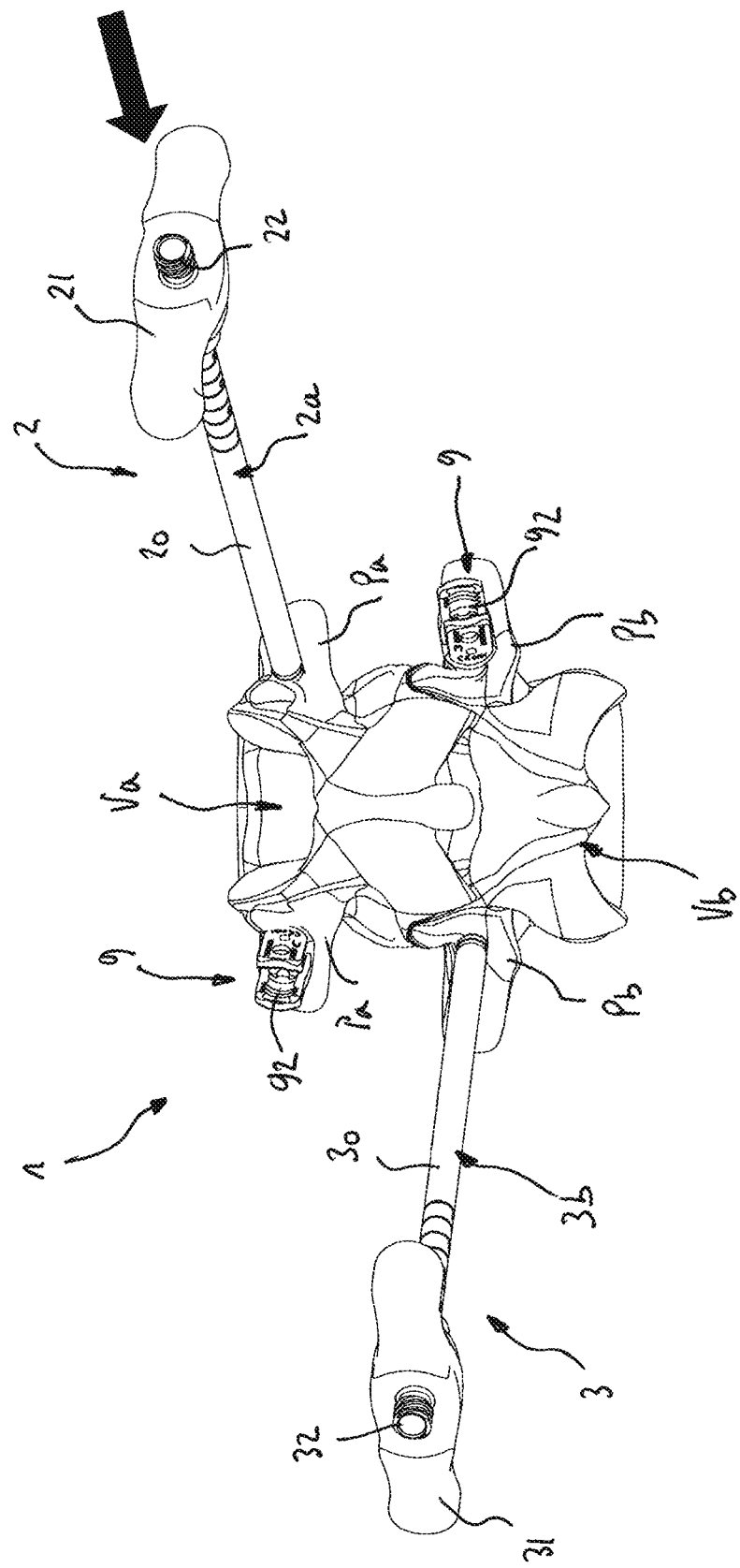
Figure 16:
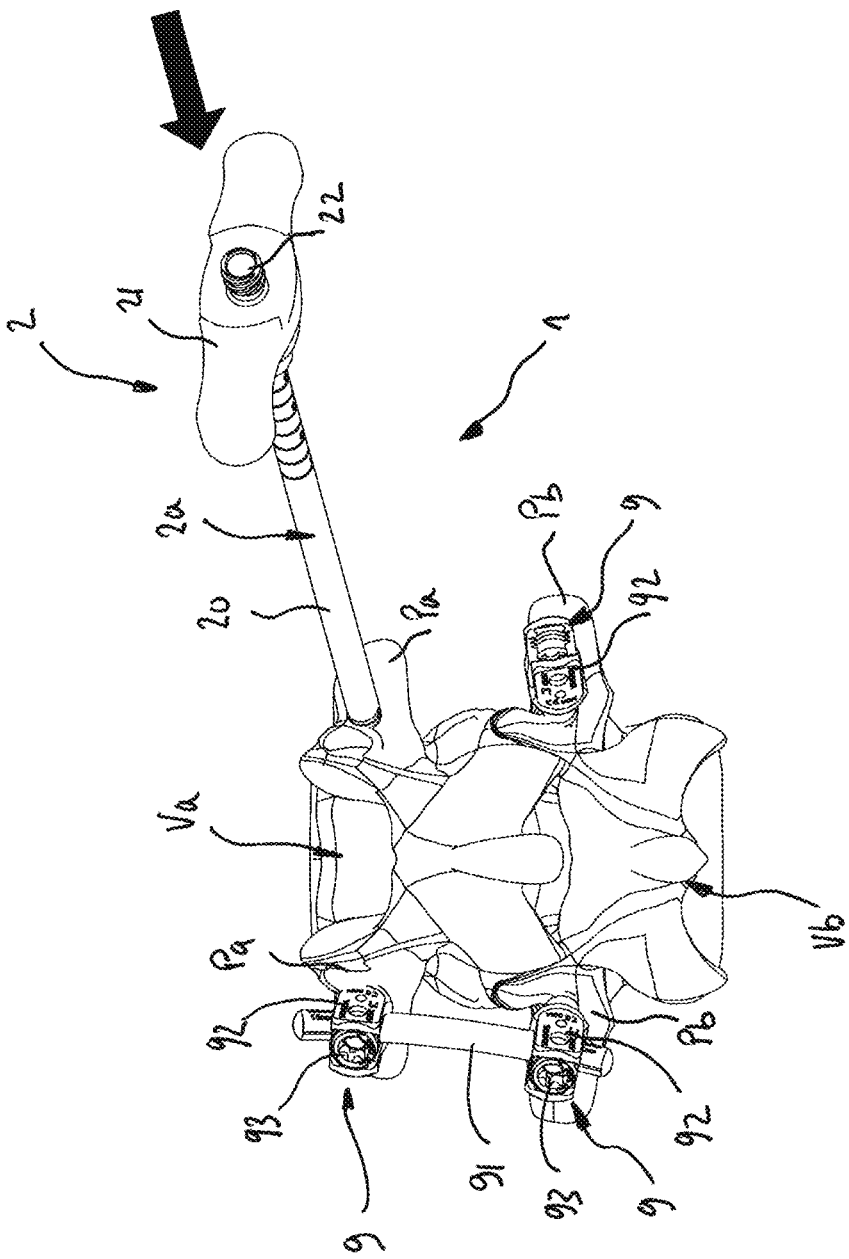

FIGS. 15 and 16 show the following steps of injection of the autologous or biological graft 8:

in screwing two closing devices 9 in place of a straight pedicular cannula 2a, 3a of the upper vertebra Va and of a straight pedicular cannula 2b, 3b of the lower vertebra Vb, in connecting an injection device 7 that has been filled beforehand with autologous or biological graft 8 onto the straight pedicular cannula 2a, 3a of the upper vertebra Va, in injecting the graft 8 through the straight pedicular cannula 2a, 3a of the upper vertebra Va in order to fill the intersomatic space Es and to the point said graft overflows through the straight pedicular cannula 2b, 3b of the lower vertebra Vb, in screwing a third closing device 9 in place of the straight pedicular cannula 2b, 3b of the lower vertebra Vb, in connecting the closing devices 9 located one above the other and rigidly connected to the vertebrae Va, Vb by a first linking device, in continuing the injection of the graft 8 with a pressurization in order to restore the disk height between the vertebrae Va, Vb, in immobilizing in translation and rotation the first linking device in the closing devices 9, in disconnecting the injection device (7) and in withdrawing the last straight pedicular cannula from the upper vertebra Va for the fixation of a fourth closing device (9), and in connecting and in immobilizing the two remaining closing devices (9) by a second linking device.

Figure 17:
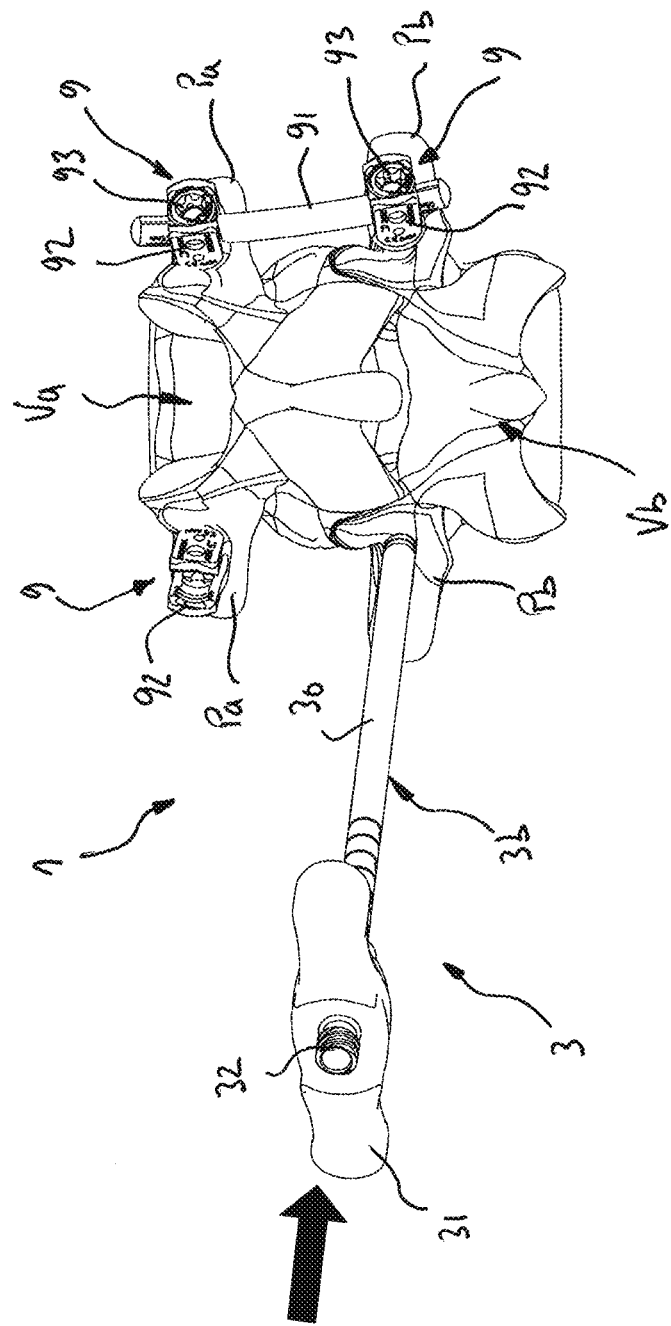
Figure 18:
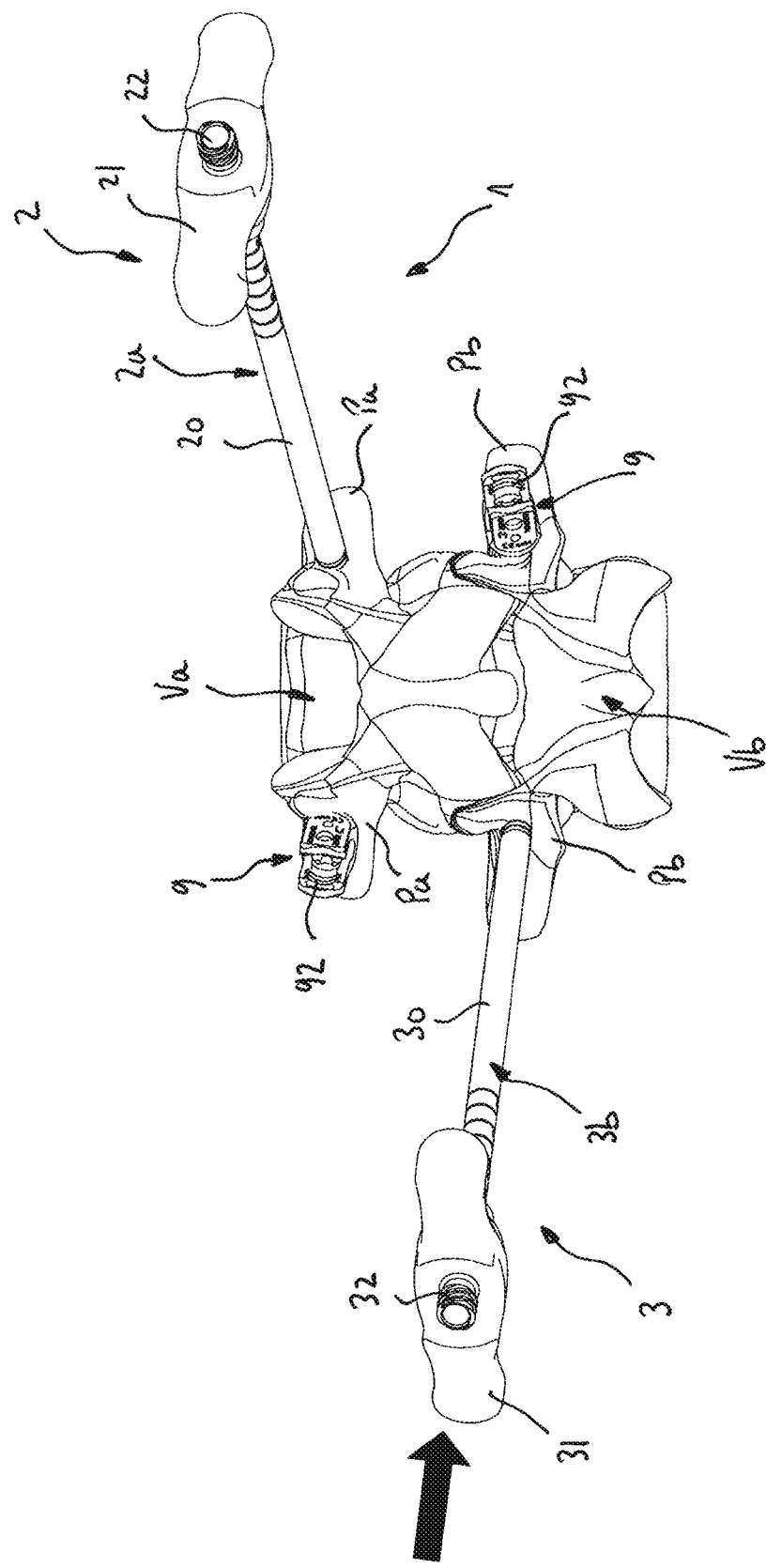

FIGS. 17 and 18 represent the following steps of injection of the autologous or biological graft 8:

in screwing two closing devices 9 in place of a straight pedicular cannula 2a, 3a of the upper vertebra Va and of a straight pedicular cannula 2b, 3b of the lower vertebra Vb, in connecting an injection device 7 that has been filled beforehand with autologous or biological graft 8 onto the straight pedicular cannula 2b, 3b of the lower vertebra Vb, in injecting the graft 8 through the straight pedicular cannula 2b, 3b of the lower vertebra Vb in order to fill the intersomatic space Es and to the point that said graft overflows through the straight pedicular cannula 2a, 3a of the upper vertebra Va, in screwing a third closing device 9 in place of the straight pedicular cannula 2a, 3a of the upper vertebra Va, in connecting the closing devices 9 located one above the other and rigidly connected to the vertebrae Va, Vb by a first linking device, in continuing the injection of the graft 8 with a pressurization in order to restore the disk height between the vertebrae Va, Vb, in immobilizing in translation and rotation the first linking device in the closing devices 9, in disconnecting the injection device 7 and in withdrawing the last straight pedicular cannula from the lower vertebra Vb for the fixation of a fourth closing device 9, and in connecting and in immobilizing the two remaining closing devices 9 by a second linking device.

Figure 19:
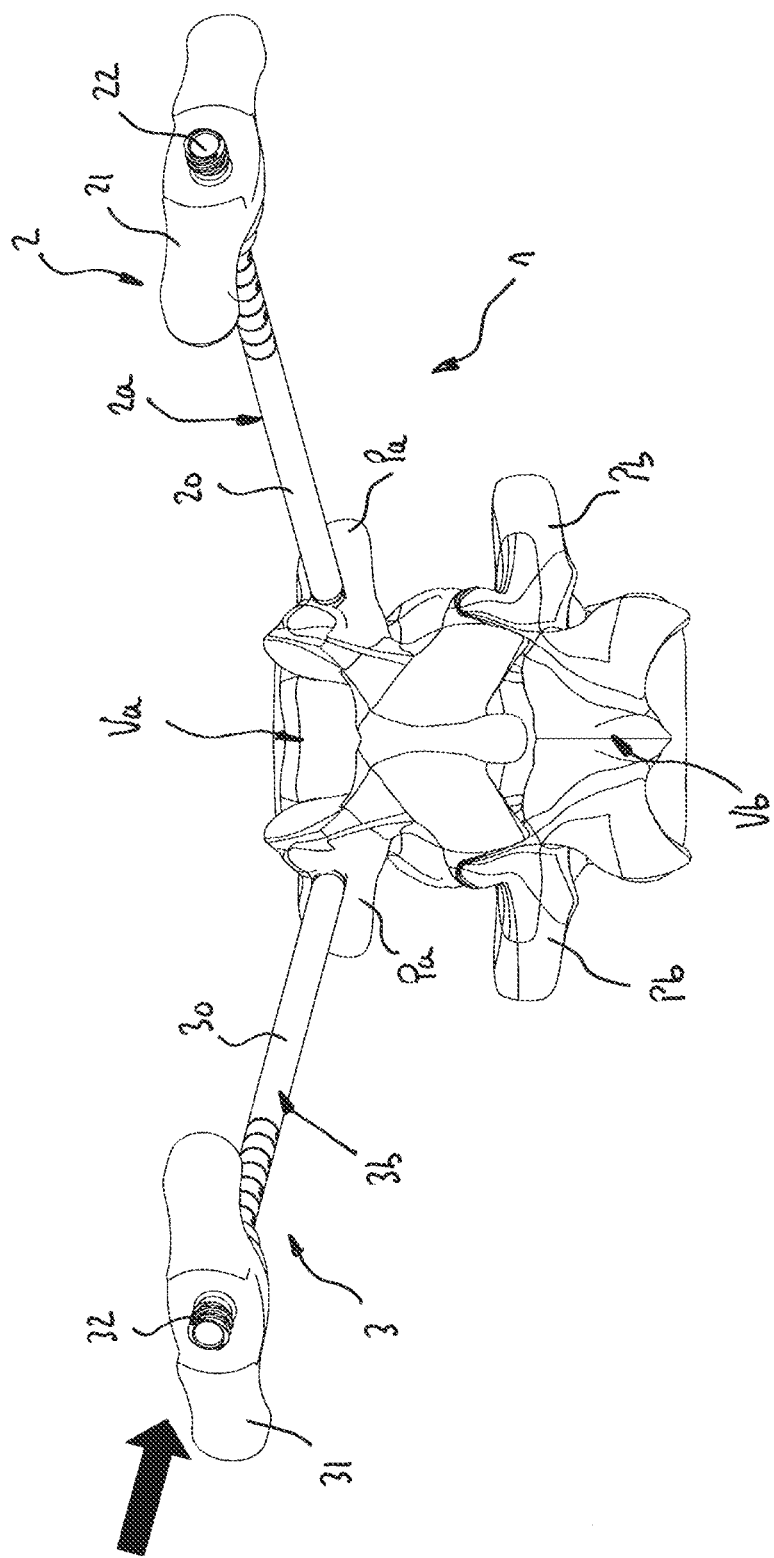
Figure 20:
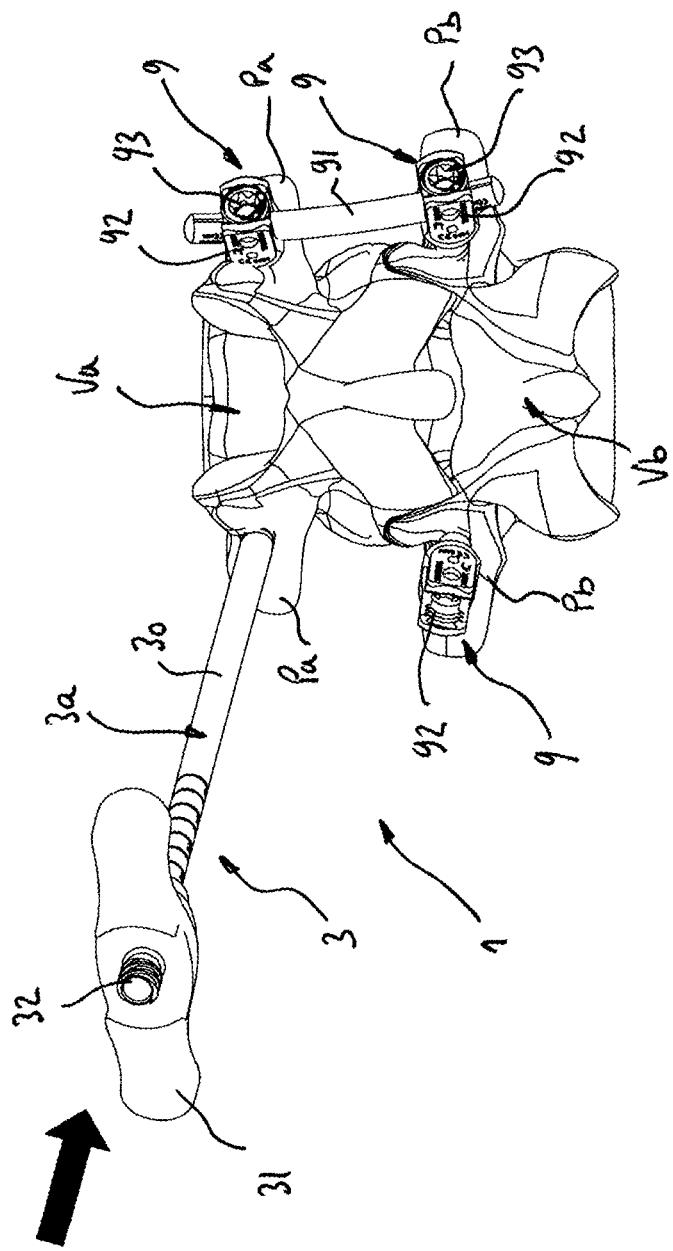

FIGS. 19 and 20 illustrate the following steps of injection of the autologous or biological graft 8:

in screwing two closing devices 9 into the pedicles Pb of the lower vertebra Vb, in connecting an injection device 7 that has been filled beforehand with autologous or biological graft 8 onto a straight pedicular cannula 2a, 3a of the upper vertebra Va, in injecting the graft 8 through one of the straight pedicular cannulas 2a, 3a of the upper vertebra Va in order to fill the intersomatic space Es and to the point said graft overflows through the other straight pedicular cannula 2a, 3a of the upper vertebra Va, in screwing a third closing device 9 in place of the straight pedicular cannula 2a, 3a of the upper vertebra Va that does not carry the injection device 7, in connecting the closing devices 9 located one above the other and rigidly connected to the vertebrae Va, Vb by a first linking device, in continuing the injection of the graft 8 with a pressurization in order to restore the disk height between the vertebrae Va, Vb, in immobilizing in translation and rotation the first linking device in the closing devices 9, in disconnecting the injection device 7 and in withdrawing the last straight pedicular cannula from the upper vertebra Va for the fixation of a fourth closing device 9, and in connecting and in immobilizing the two remaining closing devices 9 by a second linking device.

Figure 21:
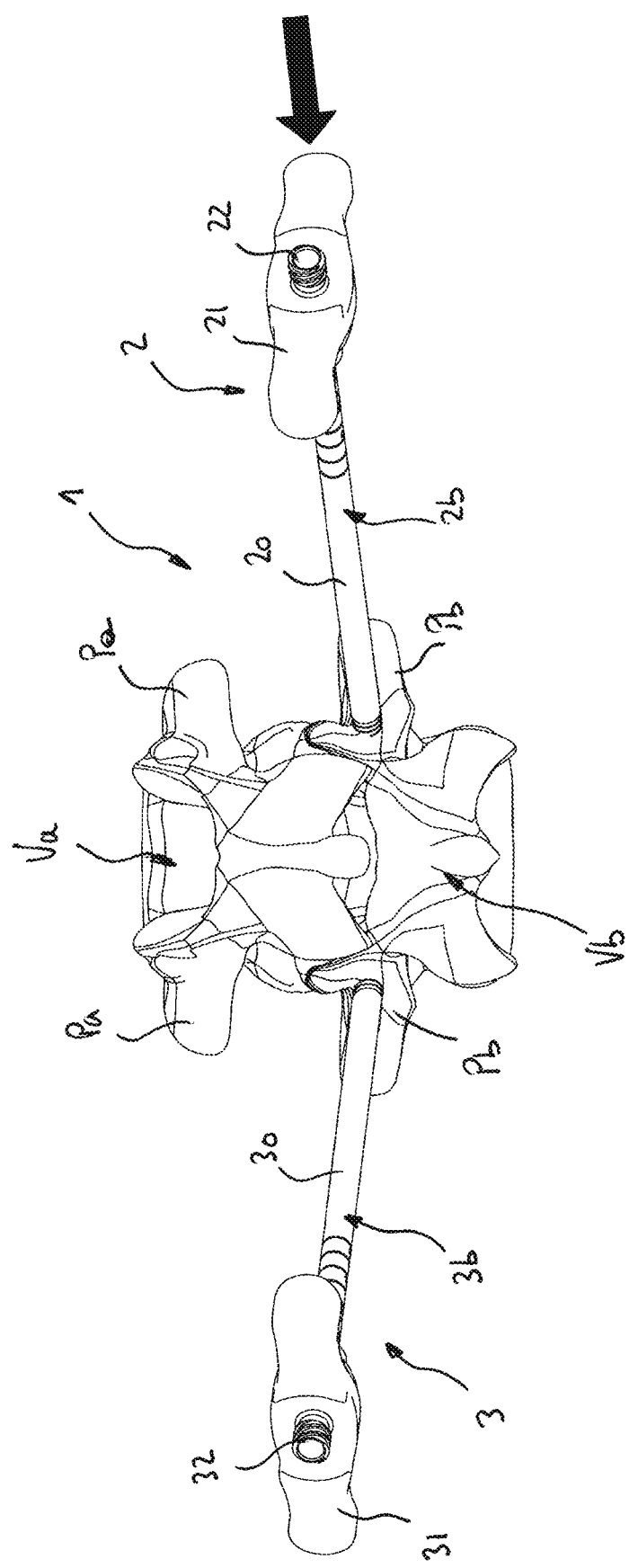
Figure 22:
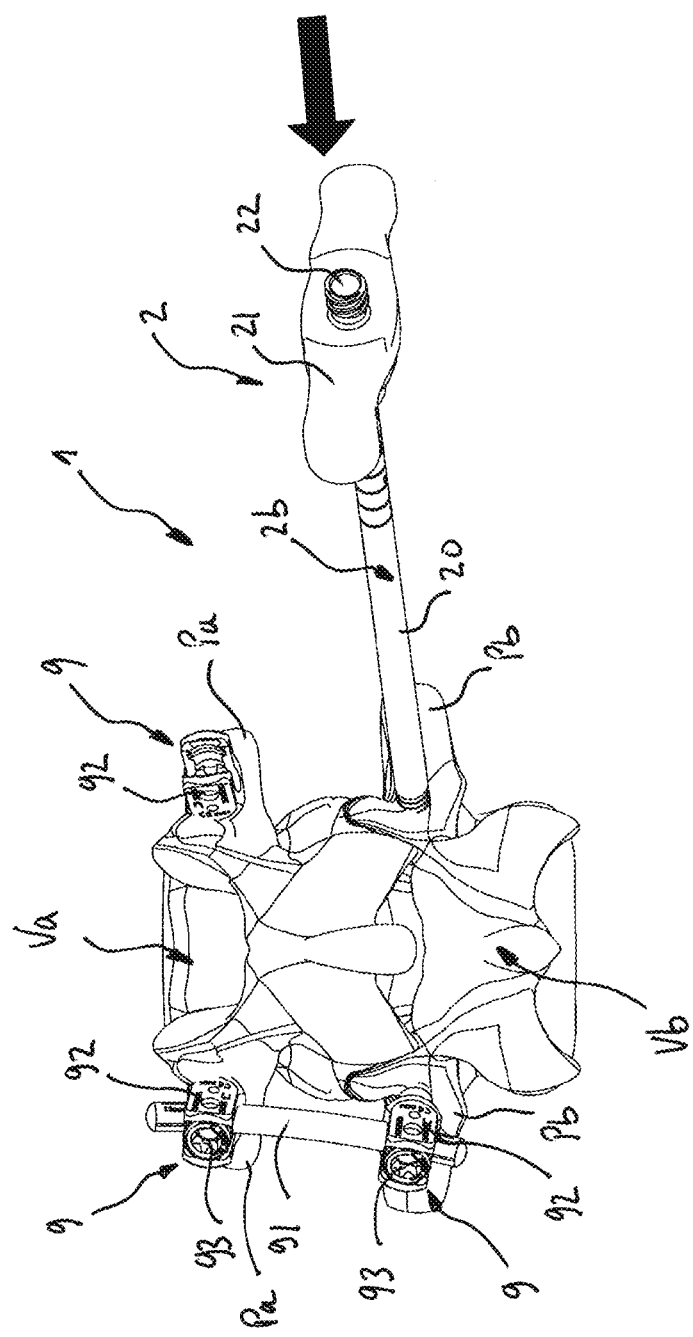

FIGS. 21 and 22 show the following steps of injection of the autologous or biological graft 8:

in screwing two closing devices 9 in the pedicles Pa of the upper vertebra Va, in connecting an injection device 7 that has been filled beforehand with autologous or biological graft 8 onto a straight pedicular cannula 2b, 3b of the lower vertebra Vb, in injecting the graft 8 through one of the straight pedicular cannulas 2b, 3b of the lower vertebra Vb in order to fill the intersomatic space Es and to the point said graft overflows through the other straight pedicular cannula 2b, 3b of the lower vertebra Vb, in screwing a third closing device 9 in place of the straight pedicular cannula 2b, 3b of the lower vertebra Vb that does not carry the injection device 7, in connecting the closing devices 9 located one above the other and rigidly connected to the vertebrae Va, Vb by a first linking device, in continuing the injection of the graft 8 with a pressurization in order to restore the disk height between the vertebrae Va, Vb, in immobilizing in translation and rotation the first linking device in the closing devices 9, in disconnecting the injection device 7 and in withdrawing the last straight pedicular cannula from the lower vertebra Vb for the fixation of a fourth closing device 9, and in connecting and in immobilizing the two remaining closing devices 9 by a second linking device.

It should be understood that the preceding description was given only as an example and that it in no way limits the scope of the invention, which one would not exceed by replacing the described implementation details with any other equivalent.

The invention claimed is:

1. Device enabling the placement and the injection of an autologous or biological graft (8) into an intersomatic space Es that has been arranged beforehand between two upper and lower vertebrae Va, Vb of a spinal segment, in order to bring about an intersomatic fusion by an entirely percutaneous transpedicular approach, wherein the device comprises:

at least one guide pin, at least two straight pedicular cannulas (2a, 3a; 2b, 3b) configured to be arranged respectively on the upper vertebra Va or on the lower vertebra Vb, or on the two vertebrae Va, Vb of the spinal segment of the at least one guide pin (4) with a curved profile, which is implanted in an endplate Pi, Ps of a corresponding vertebra Va, Vb through a corresponding pedicular cannula, a flexible cannulated drill bit (5) guided around the corresponding guide pin (4), wherein the flexible cannulated drill bit (5) comprises a rigid cannulated rod (50) extended by a flexible longitudinal area consisting of a hollow and flexible torsion cable (51) rigidly connected at a free end thereof to a cannulated bur (52) having sharp profiles, a cannulated drive system (6) including a motor configured to drive in rotation the flexible cannulated drill bit (5), wherein, on the opposite side from the cannulated bur (52), the rigid rod (50) of the cannulated drill bit (5) comprises a connection with the cannulated drive system (6) enabling the driving of said cannulated drill bit (5) in back and forth and rotation movements, wherein the curved guide pin (4) comprises a connection with the cannulated drive system (6) enabling the holding of the curved guide pin (4), controlling of the curved guide pin (4), and the application of back and forth movements to the curved guide pin (4), wherein the flexible cannulated drill bit (5) is configured to be guided around the corresponding guide pin (4) and to be driven in back and forth movements by the cannulated drive system (6) to create a set of more than one perforations in said lower endplate Pi and upper endplate Ps of each vertebra Va and/or Vb, including at least a first perforation formed by moving the flexible cannulated drill bit (5) around the curved guide pin (4), and a second perforation formed by applying the guide pin against an internal wall of the first perforation and moving the flexible cannulated drill bit (5) around the curved guide pin (4), thereby broadening the first perforation and progressively nibbling out gradually and in a controlled manner the intersomatic space Es, which is broader than the first perforation, an injection device (7) connected to one of the straight pedicular cannulas (2a, 3a; 2b, 3b) for the injection of a graft (8) into the intersomatic space Es thus produced, and closing devices (9) that are screwed into holes left free after the retraction of said straight pedicular cannulas.

2. Device according to claim 1, wherein the closing devices (9) are pedicular screws (90) of a spinal fixation device making it possible to place and fix linking rods (91).

3. Device according to claim 2, wherein each pedicular screw (90) comprises a linking connector (92) that cooperates with a set screw (93) for the immobilization in translation and rotation of a linking rod (91).

4. A method for using the device of claim 1 by producing the intersomatic space Es by an entirely percutaneous transpedicular approach between the two upper and lower vertebrae Va, Vb of the spinal segment of a vertebral column, wherein the method comprises:

carrying out a percutaneous transpedicular sighting for placement and introduction of at least one of the at least two straight pedicular cannulas (2a, 3a; 2b, 3b) into the pedicles Pa and/or Pb of the vertebrae Va and/or Vb, introducing into the at least one of the at least two straight pedicular cannulas (2a, 3a; 2b, 3b) the at least one guide pin (4) with a curved profile that reaches the vertebral endplates Pi, Ps of the vertebrae Va, Vb, respectively, slipping the flexible cannulated drill bit (5) connected to the cannulated drive system (6) onto the curved guide pin (4), in such a manner that the flexible longitudinal area which is rigidly connected to the cannulated bur (52) of said cannulated drill bit (5) perforates by means of back and forth movements the vertebral endplates Pi and Ps to produce an intersomatic space Es, cleaning, by means of a cleaning device introduced into the at least one of the at least two straight pedicular cannulas (2a, 3a and 2b, 3b), the intersomatic space Es by injection and aspiration of a saline solution in order to remove a maximum of flaps of nucleic tissues, and withdrawing the curved pin (4) and the cleaning device from the corresponding straight pedicular cannula (2a, 3a and 2b, 3b).

5. The method of claim 4 further comprising:

placing and introducing two straight pedicular cannulas (2b, 3b) into each of the lower vertebra Vb and the upper vertebra Va, screwing two closing devices (9) in place of the two straight pedicular cannulas (2b, 3b) of the lower vertebra Vb, connecting an injection device (7) that has been filled beforehand with an autologous or biological graft (8) onto one of the straight pedicular cannulas (2a, 3a) of the upper vertebra Va, injecting the graft (8) through one of the straight pedicular cannulas (2a, 3a) in order to fill the intersomatic space Es and to the point said graft overflows through the other straight pedicular cannula of the upper vertebra Va, screwing a third closing device (9) in place of the straight pedicular cannula of the upper vertebra Va that does not carry the injection device (7), connecting the closing devices (9) located one above the other and rigidly connected to the vertebrae Va, Vb by a first linking device, continuing the injection of the graft (8) with a pressurization in order to restore a disk height between the vertebrae Va, Vb, immobilizing in translation and rotation the first linking device in the closing devices (9), disconnecting the injection device (7) and withdrawing the last straight pedicular cannula from the vertebra Va for the fixation of a fourth closing device (9), and connecting and immobilizing the two remaining closing devices (9) by a second linking device.

6. The method of claim 5 further comprising:

introducing a secure pin device (10) through one of the straight pedicular cannulas (2a, 3a; 2b, 3b) already in place up to an anterior wall of the corresponding vertebra Va, Vb, deploying a forked portion (102) of the secure pin (101) so that the latter is supported in the spongy bone of the vertebra Va, Vb, withdrawing the corresponding straight pedicular cannula (2a, 3a; 2b, 3b) from the vertebra Va, Vb, screwing a cannulated pedicular screw (90) of the closing device (9) into the body of the vertebra Va, Vb using the guidance of the secure pin (101), withdrawing the secure pin (101) through the cannulated pedicular screw (90) before the end of the screwing of the latter to the desired depth.

7. The method of claim 4 further comprising:

placing and introducing two straight pedicular cannulas (2b, 3b) into each of the lower vertebra Vb and the upper vertebra Va, screwing two closing devices (9) in place of the two straight pedicular cannulas (2a, 3a) of the upper vertebra Va, connecting an injection device (7) that has been filled beforehand with an autologous or biological graft (8) onto one of the straight pedicular cannulas (2b, 3b) of the lower vertebra Vb, injecting the graft (8) through one of the straight pedicular cannulas (2b, 3b) in order to fill the intersomatic space Es and to the point said graft overflows through the other straight pedicular cannula of the lower vertebra Vb, screwing a third closing device (9) in place of the straight pedicular cannula of the lower vertebra Vb that does not carry the injection device (7), connecting the closing devices (9) located one above the other and rigidly connected to the vertebrae Va, Vb by a first linking device, continuing the injection of the graft (8) with a pressurization in order to restore a disk height between the vertebrae Va, Vb, immobilizing in translation and rotation the first linking device in the closing devices (9), disconnecting the injection device (7) and withdrawing the last straight pedicular cannula from the lower vertebra Vb for the fixation of a fourth closing device (9), and connecting and immobilizing the two remaining closing devices (9) by a second linking device.

8. The method of claim 4 further comprising:

placing and introducing two straight pedicular cannulas (2b, 3b) into each of the lower vertebra Vb and the upper vertebra Va, screwing two closing devices (9) in place of a straight pedicular cannula (2a, 3a) of the upper vertebra Va and of a straight pedicular cannula (2b, 3b) of the lower vertebra Vb, connecting an injection device (7) that has been filled beforehand with an autologous or biological graft (8) onto the straight pedicular cannula (2a, 3a) of the upper vertebra Va, injecting the graft (8) through the straight pedicular cannula (2a, 3a) of the upper vertebra Va in order to fill the intersomatic space Es and to the point said graft overflows through the straight pedicular cannula (2b, 3b) of the lower vertebra Vb, screwing a third closing device (9) in place of the straight pedicular cannula (2b, 3b) of the lower vertebra Vb, connecting the closing devices (9) located one above the other and rigidly connected to the vertebrae Va, Vb by a first linking device, continuing the injection of the graft (8) with a pressurization in order to restore a disk height between the vertebrae Va, Vb, immobilizing in translation and rotation the first linking device in the closing devices (9), disconnecting the injection device (7) and withdrawing the last straight pedicular cannula from the upper vertebra Va for the fixation of a fourth closing device (9), and connecting and immobilizing the two remaining closing devices (9) by a second linking device.

9. The method of claim 4 further comprising:

placing and introducing two straight pedicular cannulas (2b, 3b) into each of the lower vertebra Vb and the upper vertebra Va, screwing two closing devices (9) in place of a straight pedicular cannula (2a, 3a) of the upper vertebra Va and of a straight pedicular cannula (2b, 3b) of the lower vertebra Vb, connecting an injection device (7) that has been filled beforehand with an autologous or biological graft (8) onto the straight pedicular cannula (2b, 3b) of the lower vertebra Vb, injecting the graft (8) through the straight pedicular cannula (2b, 3b) of the lower vertebra Vb in order to fill the intersomatic space Es and to the point that said graft overflows through the straight pedicular cannula (2a, 3a) of the upper vertebra Va, screwing a third closing device (9) in place of the straight pedicular cannula (2a, 3a) of the upper vertebra Va, connecting the closing devices (9) located one above the other and rigidly connected to the vertebrae Va, Vb by a first linking device, continuing the injection of the graft (8) with a pressurization in order to restore a disk height between the vertebrae Va, Vb, immobilizing in translation and rotation the first linking device in the closing devices (9), disconnecting the injection device (7) and withdrawing the last straight pedicular cannula from the lower vertebra Vb for the fixation of a fourth closing device (9), and connecting and immobilizing the two remaining closing devices (9) by a second linking device.

10. The method of claim 4 further comprising:

placing and introducing two straight pedicular cannulas (2b, 3b) into each of the lower vertebra Vb and the upper vertebra Va, screwing two closing devices (9) into the pedicles Pb of the lower vertebra Vb, connecting an injection device (7) that has been filled beforehand with an autologous or biological graft (8) onto a straight pedicular cannula (2a, 3a) of the upper vertebra Va, injecting the graft (8) through one of the straight pedicular cannulas (2a, 3a) of the upper vertebra Va in order to fill the intersomatic space Es and to the point said graft overflows through the other straight pedicular cannula (2a, 3a) of the upper vertebra Va, screwing a third closing device (9) in place of the straight pedicular cannula (2a, 3a) of the upper vertebra Va that does not carry the injection device (7), connecting the closing devices (9) located one above the other and rigidly connected to the vertebrae Va, Vb by a first linking device, continuing the injection of the graft (8) with a pressurization in order to restore a disk height between the vertebrae Va, Vb, immobilizing in translation and rotation the first linking device in the closing devices (9), disconnecting the injection device (7) and withdrawing the last straight pedicular cannula from the upper vertebra Va for the fixation of a fourth closing device (9), and connecting and immobilizing the two remaining closing devices (9) by a second linking device.

11. The method of claim 4 further comprising:

placing and introducing two straight pedicular cannulas (2*b*, 3*b*) into each of the lower vertebra Vb and the upper vertebra Va, screwing two closing devices (9) in the pedicles Pa of the upper vertebra Va, connecting an injection device (7) that has been filled beforehand with an autologous or biological graft (8) onto a straight pedicular cannula (2*b*, 3*b*) of the lower vertebra Vb, injecting the graft (8) through one of the straight pedicular cannulas (2*b*, 3*b*) of the lower vertebra Vb in order to fill the intersomatic space Es and to the point said graft overflows through the other straight pedicular cannula (2*b*, 3*b*) of the lower vertebra Vb, screwing a third closing device (9) in place of the straight pedicular cannula (2*b*, 3*b*) of the lower vertebra Vb that does not carry the injection device (7), connecting the closing devices (9) located one above the other and rigidly connected to the vertebrae Va, Vb by a first linking device, continuing the injection of the graft (8) with a pressurization in order to restore a disk height between the vertebrae Va, Vb, immobilizing in translation and rotation the first linking device in the closing devices (9), disconnecting the injection device (7) and withdrawing the last straight pedicular cannula from the lower vertebra Vb for the fixation of a fourth closing device (9), and connecting and immobilizing the two remaining closing devices (9) by a second linking device.

* * * * *